(12) United States Patent
Townsend et al.

(10) Patent No.: US 9,139,588 B2
(45) Date of Patent: Sep. 22, 2015

(54) METHOD FOR LATE INTRODUCTION OF THE (8R)-HYDROXYL GROUP CARBAPENEM β-LACTAM ANTIBIOTIC SYNTHESIS

(75) Inventors: Craig Arthur Townsend, Baltimore, MD (US); Micah Jeffrey Bodner, Dexter, OR (US); Ryan Martin Phelan, Baltimore, MD (US); Michael Francis Freeman, Baltimore, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 0 days.

(21) Appl. No.: 13/515,114

(22) PCT Filed: Dec. 13, 2010

(86) PCT No.: PCT/US2010/060081
§ 371 (c)(1),
(2), (4) Date: Oct. 29, 2012

(87) PCT Pub. No.: WO2011/072287
PCT Pub. Date: Jun. 16, 2011

(65) Prior Publication Data
US 2013/0066066 A1    Mar. 14, 2013

Related U.S. Application Data

(60) Provisional application No. 61/285,608, filed on Dec. 11, 2009.

(51) Int. Cl.
*C07D 477/20* (2006.01)
*C12P 17/18* (2006.01)

(52) U.S. Cl.
CPC ............ *C07D 477/20* (2013.01); *C12P 17/184* (2013.01)

(58) Field of Classification Search
CPC .................................................. C07D 477/20
USPC ................................................. 540/302, 350
See application file for complete search history.

(56) References Cited

U.S. PATENT DOCUMENTS

| 4,235,922 | A | | 11/1980 | Ratcliffe et al. | |
|---|---|---|---|---|---|
| 4,374,144 | A | | 2/1983 | Corbett | |
| 4,839,352 | A | * | 6/1989 | Barash et al. | 210/210 |
| 2004/0038250 | A1 | | 2/2004 | Nunez et al. | |

OTHER PUBLICATIONS

Freeman et al. PNAS (2008), vol. 105, No. 32 11128-11133.*
Freeman, Michael F. PNAS 105(32) 11128-11133, Aug. 2008.*
Nunez, Luz Elena. Chemistry & Biology, vol. 10, 301-311, Apr. 2003.*
Extended European Search Report dated Apr. 8, 2013 from European Application No. EP 10 83 6801.
Coulthurst S. J. et al: "Regulation and biosynthesis of carbapenem antibiotics in bacteria", Nature Reviews. Microbiology, Nature Publishing Group, GB, vol. 3, No. 4, Apr. 1, 2005, pp. 295-306, XP008159336, ISSN: 1740-1526, DOI: 10.1038/NRMICR01128 [retrieved on Mar. 10, 2005].
Box S.J. et al: "Four further antibiotics related to olivanic acid produced by *Streptomyces olivaceus*: Fermentation, isolation, characterisation and biosynthetic studies", Journal of Antibiotics, Japan Antibiotics Research Association, Tokyo, JP, vo 1 • 32. No. 12, Jan. 1, 1979, pp. 1239-1247, XP009168266, ISSN: 0021-8820.
Okabe M. et al: "Preferential production of a carbapenem antibiotic, PS-5 by dissolved oxygen controlled fermentation", Journal of Fermentation and Bioengineering, Society of Fermentation Technology, JP, vol. 70, No. 1, Jan. 1, 1990, pp. 30-33, XP023554426, ISSN: 0922-338X, DOI: 10.1016/0922-338X(90)90026-S [retrieved on Jan. 1, 1990].
Cardwell K. et al: "Methods for Indole Alkaloid Synthesis. Compatibility of the 16-Methoxy Substituent with the Indole-2,3-Quinodimethane Strategy to Aspidosperma-Type Indole Alkaloids", Tetrahedron Letters, vol. 28, No. 29, Jan. 1, 1987, pp. 3303-3386, XP055057554, ISSN: 0040-4839.
Iimori T. The American Chemical Society, vol. 105, No. 6, Mar. 1, 1983, pp. 1659-1660, XP055057692, ISSN: 0002-7863, DOI: 10.1021/ja00344a044.

* cited by examiner

*Primary Examiner* — Golam M M Shameem
*Assistant Examiner* — Laura Daniel
(74) *Attorney, Agent, or Firm* — Ward and Smith, P.A.

(57) ABSTRACT

The presently disclosed subject matter demonstrates that ThnG and ThnQ enzymes encoded by the thienamycin gene cluster in *Streptomyces cattleya* oxidize the C-2 and C-6 moieties of carbapenems, respectively. ThnQ stereospecifically hydroxylates PS-5 giving N-acetyl thienamycin. ThnG catalyzes sequential desaturation and sulfoxidation of PS-5, giving PS-7 and its sulfoxide. The ThnG and ThnQ enzymes are relatively substrate selective, but give rise to the oxidative diversity of carbapenems produced by *S. cattleya*, and orthologues likely function similarly in allied *streptomyces*.

3 Claims, 10 Drawing Sheets

SEQUENCE LISTING

```
<160> NUMBER OF SEQ ID NOS: 8

<210> SEQ ID NO 1
<211> LENGTH: 27
<212> TYPE: DNA
<213> ORGANISM: Streptomyces cattleya
<220> FEATURE:
<221> NAME/KEY: misc_feature
<223> OTHER INFORMATION: thnQ forward primer

<400> SEQUENCE: 1
gccaagcttt cacccgccgc ggaccag                                    27

<210> SEQ ID NO 2
<211> LENGTH: 30
<212> TYPE: DNA
<213> ORGANISM: Streptomyces cattleya
<220> FEATURE:
<221> NAME/KEY: misc_feature
<223> OTHER INFORMATION: thnQ reverse primer

<400> SEQUENCE: 2
cactaactcg agcccgccgc ggaccaggtc                                 30

<210> SEQ ID NO 3
<211> LENGTH: 29
<212> TYPE: DNA
<213> ORGANISM: Streptomyces cattleya
<220> FEATURE:
<221> NAME/KEY: misc_feature
<223> OTHER INFORMATION: thnG forward primer

<400> SEQUENCE: 3
ctagtctaga ggcctcctcg gcggagaag                                  29

<210> SEQ ID NO 4
<211> LENGTH: 29
<212> TYPE: DNA
<213> ORGANISM: Streptomyces cattleya
<220> FEATURE:
<221> NAME/KEY: misc_feature
<223> OTHER INFORMATION: thnG reverse primer

<400> SEQUENCE: 4
ttataagctt tggccatggt gaacggctg                                  29
```

<210> SEQ ID NO 5
<211> LENGTH: 780
<212> TYPE: DNA
<213> ORGANISM: Streptomyces cattleya
<220> FEATURE:
<221> NAME/KEY: misc_feature
<223> OTHER INFORMATION: Nucleotide Sequence for thnQ

<400> SEQUENCE: 5

```
atgaccgcct cacatgacac ggcagacgcc acggaccgga ccgtcggttc cacgtccggc      60
gaacgagcgg cgttcgcccg tgacggagtg gtgcgttggg gccgcctgct gacgcctgat     120
cagatcgacg cgctgcggtc ctcggtggag cgtgccttct ccgcgacgg ccaccccgcc     180
gacggggtac gcgatctgtc cgaacgccag ggccgcccgc tcgacctggc cctgctgcac     240
aagatcaacc tgtggcggac cgacgaggcg tgcgcggccc aggtggccag ggccgacctg     300
gcggaccggg ccgaggcgct gctcggcggg ccggtacggc tctaccgcga ccacgtcttc     360
tacaagccgc cgggcaaggg cgaccgcagc cgcatggtgc tccaccagga caaccgctac     420
tggcacctgg acccgccgga ggccatcacg gtgtggatgg cgctggacga cgccaccgtg     480
gagaacgggt gcgtccacta cgtcctcggc agccaccgcc acggcgggt ggagcacgtg     540
cgtcccgagg agggcgcggt gatgatcgag gcccgtaccg agcaggagcc ggtggcctac     600
ccggcccccg ccggggacgc cctggtgcac agcgtcaaca cgctgcacgg ctcggggccc     660
aacctcagcg acggaccgcg ccgcgcctac gtggtggtct acgtgcgcga cggggtgacg     720
atgcgcggcg agccgatgac ctcgttcccg ctcgtcggcg acctggtccg cggcgggtga     780
```

<210> SEQ ID NO 6
<211> LENGTH: 792
<212> TYPE: DNA
<213> ORGANISM: Streptomyces cattleya
<220> FEATURE:
<221> NAME/KEY: misc_feature
<223> OTHER INFORMATION: Nucleotide Sequence for thnG

<400> SEQUENCE: 6

```
tcaccgtccg ctctccggcc cggcggggtg gcggggcagc gaatagcagt aggagacggc      60
acgccggtcg tcctcggtgg tgttgggcgc cgaggtgtgg gcgacgtagc cgttgaacag     120
cagcgccgag ccggccttgc ggggcagggt gaccggggtg aggccgggcc agatgcgtgc     180
gatgtccagg gacggttcgc gcggtgaggc gaagatgtcg ccggggtcga tgccgtccgg     240
ttcgtagagt ttgcgttccc ggtgggagcc gggcaggaag cgcaggcagc cgttgtcctc     300
gcgggcgtcg tccaccgcga tccagatggt gtagacgtcc acgtacttct cgtgccactc     360
gtcggccagg aagatggcgt cctggtgcca gggtttctgg gagccgaccc gggagggctt     420
ggcccacagg aagcagtcgt agaagtcacc gggcaggccg tgcagcggtt cgatcagctt     480
ctcgttgagg ccgacgaggt cggggacggc ggcgaggtcg gcggagtgtt cgtgggcgcg     540
gccgatgatg cgcaccttgc cgggtatgca ctccttgccg gccgcccggg cggcccatcc     600
gccgccctcc ccctcggcct ccagctgcca ttcctcggtg ctgatgcgca tccgctcggt     660
gcggccgatc agttcggcgc agccgcgcg catcaccctcg agtacggatt cgggcaccag     720
gtcgtccagc gccacgacac cgtcgcgccg cagttcgtcg acagggcct ggatcgactg     780
ggtcaccggc at                                                         792
```

<210> SEQ ID NO 7

<211> LENGTH: 259
<212> TYPE: PRT
<213> ORGANISM: Streptomyces cattleya
<220> FEATURE:
<221> NAME/KEY: MISC_FEATURE
<223> OTHER INFORMATION: Amino Acid Sequence for thnQ
<300> PUBLICATION INFORMATION:
<308> DATABASE ACCESSION NUMBER: CAD18985.1
<309> DATABASE ENTRY DATE: 2005-04-15
<313> RELEVANT RESIDUES IN SEQ ID NO: (1)..(259)

<400> SEQUENCE: 7

Met Thr Ala Ser His Asp Thr Ala Asp Ala Thr Asp Arg Thr Val Gly
1               5                   10                  15

Ser Thr Ser Gly Glu Arg Ala Ala Phe Ala Arg Asp Gly Val Val Arg
            20                  25                  30

Trp Gly Arg Leu Leu Thr Pro Asp Gln Ile Asp Ala Leu Arg Ser Ser
        35                  40                  45

Val Glu Arg Ala Phe Phe Arg Asp Gly His Pro Ala Asp Gly Val Arg
    50                  55                  60

Asp Leu Ser Glu Arg Gln Gly Arg Pro Leu Asp Ala Leu Leu His
65                  70                  75                  80

Lys Ile Asn Leu Trp Arg Thr Asp Glu Ala Cys Ala Ala Gln Val Ala
                85                  90                  95

Arg Ala Asp Leu Ala Asp Arg Ala Glu Ala Leu Leu Gly Gly Pro Val
            100                 105                 110

Arg Leu Tyr Arg Asp His Val Phe Tyr Lys Pro Pro Gly Lys Gly Asp
        115                 120                 125

Arg Ser Arg Met Val Leu His Gln Asp Asn Arg Tyr Trp His Leu Asp
    130                 135                 140

Pro Pro Glu Ala Ile Thr Val Trp Met Ala Leu Asp Asp Ala Thr Val
145                 150                 155                 160

Glu Asn Gly Cys Val His Tyr Val Leu Gly Ser His Arg His Gly Arg
                165                 170                 175

Val Glu His Val Arg Pro Glu Glu Gly Ala Val Met Ile Glu Ala Arg
            180                 185                 190

Thr Glu Gln Glu Pro Val Ala Tyr Pro Ala Pro Ala Gly Asp Ala Leu
        195                 200                 205

Val His Ser Val Asn Thr Leu His Gly Ser Gly Pro Asn Leu Ser Asp
    210                 215                 220

Gly Pro Arg Arg Ala Tyr Val Val Tyr Val Arg Asp Gly Val Thr
225                 230                 235                 240

Met Arg Gly Glu Pro Met Thr Ser Phe Pro Leu Val Gly Asp Leu Val
                245                 250                 255

Arg Gly Gly

<210> SEQ ID NO 8
<211> LENGTH: 263
<212> TYPE: PRT
<213> ORGANISM: Streptomyces cattleya
<220> FEATURE:
<221> NAME/KEY: MISC_FEATURE
<223> OTHER INFORMATION: Amino Acid Sequence for thnG
<300> PUBLICATION INFORMATION:
<308> DATABASE ACCESSION NUMBER: CAD18975.1
<309> DATABASE ENTRY DATE: 2005-04-15
<313> RELEVANT RESIDUES IN SEQ ID NO: (1)..(263)

<400> SEQUENCE: 8

Met Pro Val Thr Gln Ser Ile Gln Ala Leu Ser Asp Glu Leu Arg Arg

```
1               5                  10                 15
Asp Gly Val Val Ala Leu Asp Asp Leu Val Pro Glu Ser Val Leu Glu
            20                 25                 30
Val Met Arg Arg Gly Cys Ala Glu Leu Ile Gly Arg Thr Glu Arg Met
        35                 40                 45
Arg Ile Ser Thr Glu Glu Trp Gln Leu Glu Ala Glu Gly Glu Gly Gly
    50                 55                 60
Gly Trp Ala Ala Arg Ala Ala Gly Lys Glu Cys Ile Pro Gly Lys Val
65                 70                 75                 80
Arg Ile Ile Gly Arg Ala His Glu His Ser Ala Asp Leu Ala Ala Val
            85                 90                 95
Pro Asp Leu Val Gly Leu Asn Glu Lys Leu Ile Glu Pro Leu His Gly
            100                105                110
Leu Pro Gly Asp Phe Tyr Asp Cys Phe Leu Trp Ala Lys Pro Ser Arg
            115                120                125
Val Gly Ser Gln Lys Pro Trp His Gln Asp Ala Ile Phe Leu Ala Asp
            130                135                140
Glu Trp His Glu Lys Tyr Val Asp Val Tyr Thr Ile Trp Ile Ala Val
145                150                155                160
Asp Asp Ala Arg Glu Asp Asn Gly Cys Leu Arg Phe Leu Pro Gly Ser
            165                170                175
His Arg Glu Arg Lys Leu Tyr Glu Pro Asp Gly Ile Asp Pro Gly Asp
            180                185                190
Ile Phe Ala Ser Pro Arg Glu Pro Ser Leu Asp Ile Ala Arg Ile Trp
            195                200                205
Pro Gly Leu Thr Pro Val Thr Leu Pro Arg Lys Ala Gly Ser Ala Leu
            210                215                220
Leu Phe Asn Gly Tyr Val Ala His Thr Ser Ala Pro Asn Thr Thr Glu
225                230                235                240
Asp Asp Arg Arg Ala Val Ser Tyr Cys Tyr Ser Leu Pro Arg His Pro
            245                250                255
Ala Gly Pro Glu Ser Gly Arg
            260
```

METHOD FOR LATE INTRODUCTION OF THE (8R)-HYDROXYL GROUP CARBAPENEM β-LACTAM ANTIBIOTIC SYNTHESIS

CROSS-REFERENCE TO RELATED APPLICATIONS

This application claims the benefit of U.S. Provisional Application No. 61/285,608, filed Dec. 11, 2009; which is incorporated herein by reference in its entirety.

FEDERALLY SPONSORED RESEARCH OR DEVELOPMENT

This invention was made in part with United States government support under AI014937 awarded by the National Institutes of Health (NIH). The government has certain rights in the invention.

REFERENCE TO SEQUENCE LISTING SUBMITTED ELECTRONICALLY

The official copy of the Sequence Listing is submitted concurrently with the specification as an ASCII formatted text file via EFS-Web, with a file name of Sequence_Listing_for_P10954-02_ST25.txt_, creation date of Dec. 13, 2010, and a file size of 8,456 bytes. The Sequence Listing filed via EFS-Web is part of the specification and is herein incorporated by reference in its entirety.

BACKGROUND

Carbapenems are a clinically important antibiotic family. More than 50 naturally occurring carbapenam/ems are known and are distinguished primarily by their C-2/C-6 side chains where many are only differentiated by the oxidation states of these substituents. With a limited palette of variations, the carbapenem family comprises a natural combinatorial library and C-2/C-6 oxidation is associated with increased efficacy.

The (8R)-hydroxyl group historically is a troublesome feature of synthetic routes to clinically-used carbapenem β-lactam antibiotics. Unlike other commonly-used members of this antibiotic family (e.g., penicillins, cephalosporins, and clavulanic acid), which are wholly or partially fermentation products, carbapenems are produced commercially by entirely synthetic means and, as a consequence, are expensive to produce.

SUMMARY

In one aspect, the presently disclosed subject matter provides a process for preparing a carbapenem of Formula (I):

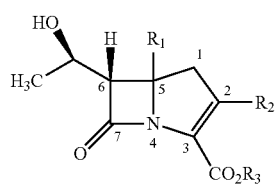

(I)

the process comprising contacting or incubating a carbapenem substrate of Formula (Ia):

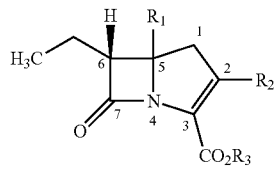

(Ia)

with a ThnQ enzyme under reaction conditions to produce the carbapenem of Formula (I); wherein: $R_1$ is H; $R_2$ is selected from the group consisting of —$SCH_2CH_2NH_2$, —SCH=CHNHC(=O)$CH_3$, —S-pantethienyl, —$SCH_2CH_2$NHC(=O)R', wherein R' is $C_1$-$C_{10}$ substituted or unsubstituted linear or branched alkyl, which can be further substituted with one or more 3-6 member cycloalkyl rings, or aminoalkyl, e.g., aminopropryl; wherein, in some embodiments, —C(=O)R' is selected from the group consisting of glycyl, beta-alanyl, 2-hydroxyacetyl, 2-methoxyacetyl, 3-hydroxypropionyl, 4-hydroxybutanoyl, and 3,4-dihydroxybutanoyl; and $R_3$ is H.

In another aspect, the presently disclosed subject matter provides a process for preparing a carbapenem of Formula (II):

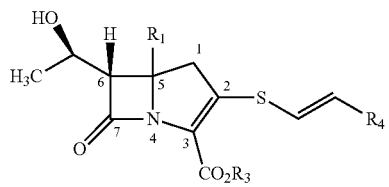

(II)

the process comprising contacting or incubating a carbapenem substrate of Formula (IIa):

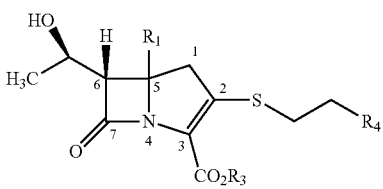

(IIa)

with a ThnG enzyme under reaction conditions to produce the carbapenem of Formula (II); wherein: $R_1$ is H; $R_2$ is selected from the group consisting of, —NH-glycyl, —NH-beta-alanyl, —NHC(=O)$CH_2CH_2CH_2NH_2$, —NH-pantethenic acid amide, acyl groups comprising $C_1$-$C_{10}$ substituted and unsubstituted linear and branched alkyl, which in some embodiments can further comprise one or more 3-6 member cycloalkyl rings, 2-hydroxyacetyl, 2-methoxyacetyl, 3-hydroxypropionyl, 4-hydroxybutanoyl, 3,4-dihydroxybutanoyl; and $R_3$ is H.

In yet another aspect, the presently disclosed subject matter provides a process for preparing a carbapenem of Formula (III):

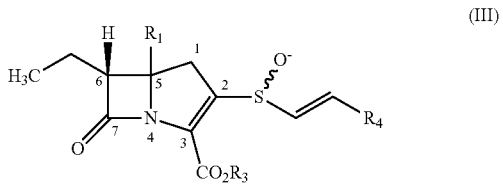

(III)

the process comprising contacting or incubating a carbapenem substrate of Formula (IIIa):

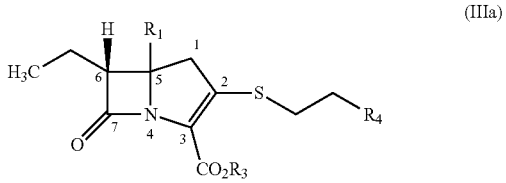

(IIIa)

with a ThnG enzyme under reaction conditions to produce a carbapenem of Formula (IIIb):

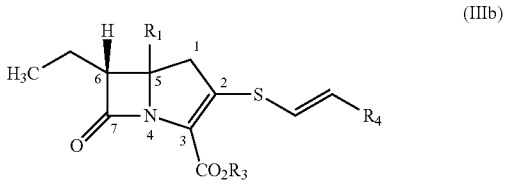

(IIIb)

then contacting or incubating the carbapenem of Formula (IIIb) with a ThnG enzyme under reaction conditions to produce a carbapenem of Formula (III); wherein: $R_1$ is H; $R_2$ is selected from the group consisting of —NH-glycyl, —NH-beta-alanyl, —NHC(=O)CH$_2$CH$_2$CH$_2$NH$_2$, —NH-pantethenic acid amide, acyl groups comprising $C_1$-$C_{10}$ substituted and unsubstituted linear and branched alkyl, which in some embodiments can further comprise one or more 3-6 member cycloalkyl rings, 2-hydroxyacetyl, 2-methoxyacetyl, 3-hydroxypropionyl, 4-hydroxybutanoyl, 3,4-dihydroxybutanoyl; and $R_3$ is H.

Certain aspects of the presently disclosed subject matter having been stated hereinabove, which are addressed in whole or in part by the presently disclosed subject matter, other aspects will become evident as the description proceeds when taken in connection with the accompanying Examples and Figures as best described herein below.

BRIEF DESCRIPTION OF THE FIGURES

Figure 1:
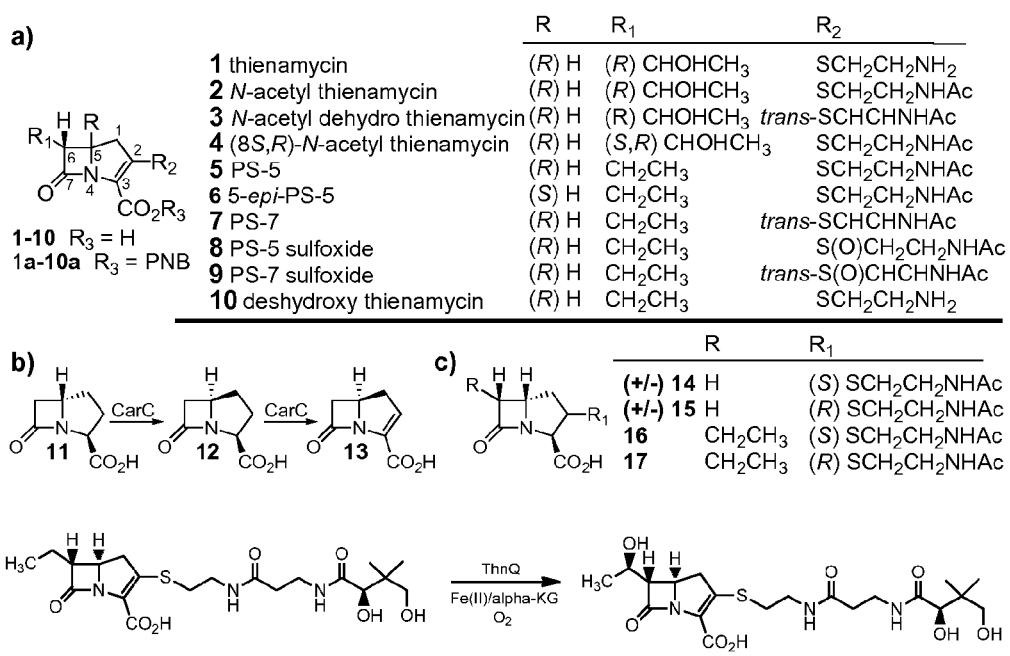

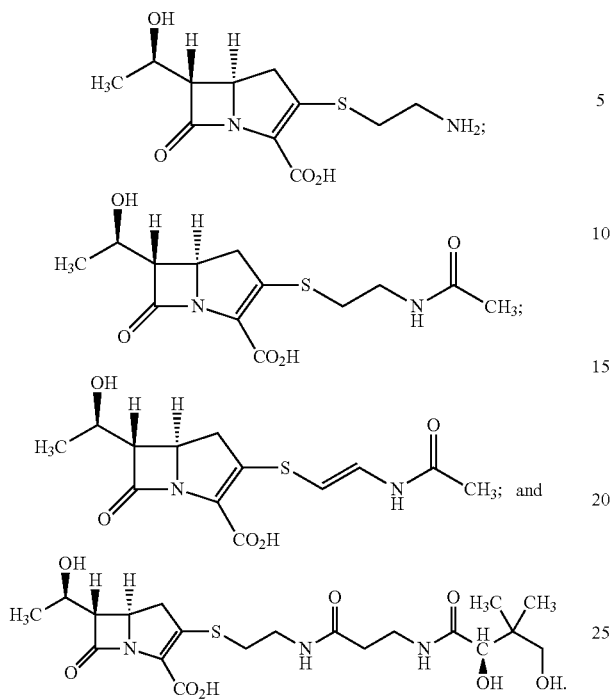

Having thus described the presently disclosed subject matter in general terms, reference will now be made to the accompanying Figures, which are not necessarily drawn to scale, and wherein:

FIGS. 1a-1c are (a) representative carbapenems; (b) the presently disclosed CarC-catalyzed reaction; and (c) representative carbapenam thioethers synthesized by the presently disclosed methods;

FIGS. 2a-2e show HPLC analysis of ThnG and ThnQ reactions with PS-5 (5): (a) PS-7 sulfoxide diasteriomers standard (9); (b) PS-7 standard (7); (c) ThnG-catalyzed reaction with 5; (d) N-Acetyl thienamycin standard (2); and (e) ThnQ-catalyzed reaction with 5;

FIGS. 3a-3i show purification of ThnG. Lanes: (a) uninduced cells; (b) induced cells; (c) molecular weight markers; (d) cell free extract; (e) insoluble cell debris; (f) Ni-NTA column flow through; (g) wash with lysis buffer; (h) wash with lysis buffer containing 20 mM imidazole; and (i) elution with lysis buffer containing 250 mM imidazole;

FIGS. 4a-4i show purification of ThnQ. Lanes: (a) uninduced cells; (b) induced cells; (c) cell free extract; (d) insoluble cell debris; (e) molecular weight markers; (f) Ni-NTA column flow through; (g) wash with lysis buffer; (h) wash with lysis buffer containing 20 mM imidazole; and (i) elution with lysis buffer containing 250 mM imidazole;

FIGS. 5a-5d show HPLC (method 1) and ESI analysis of the ThnQ-catalyzed reaction with PS5 (5). Ascending HPLC traces are offset by 30 s. (a) PS-5 (5) standard, 12.7 mM, $C_{13}H_{17}N_2O_4S$— theoretical (m/z 297.09), observed (m/z 297.10); (b) N-acetyl thienamycin standard (2), 9.4 min, $C_{13}H_{17}N_2O_5S$— theoretical (m/z 313.09), observed (m/z 313.02); (c) the ThnQ-catalyzed reaction with PS-5 (5) 9.4 min peak, observed (m/z 313.05); and (d) co-injection of N-acetyl thienamycin (2) and the ThnQ-catalyzed reaction with PS-5 (5);

FIGS. 6a-6c show HPLC (method 1) analysis of the ThnQ-catalyzed reaction with PS-5 (5) for production of other C8 diasteriomers. Ascending HPLC traces are offset by 30 s: (a) (8S,R)-N-acetyl thienamycin standard (4), 9.4, 9.5 min; (b) co-injection of (8S,R)-N-acetyl thienamycin (4) and the ThnQ-catalyzed reaction with PS-5 (5); and (c) co-injection of (8S,R)-N-acetyl thienamycin (4) and N-acetyl thienamycin (2);

FIG. 7a-7e show HPLC (method 1) and ESI analysis of the ThnG-catalyzed reaction with PS-5 (5). Ascending HPLC traces are offset by 30 s. (a) PS-7 (7) standard, 14.9 min, $C_{13}H_{15}N_2O_4S$— theoretical (m/z 295.08), observed (m/z 295.16); (b) PS-7 sulfoxide diasteriomers (9) standard, 12.3, 12.4 min, $C_{13}H_{15}N_2O_5S$— theoretical (m/z 311.07), observed (m/z 311.27); (c) the ThnG-catalyzed reaction with PS-5 (5), 12.4 min peak, observed (m/z 311.15), 14.9 min peak, observed (m/z 295.05); (d) co-injection of the ThnG-catalyzed reaction with PS-5 (5) and the PS-7 (7) standard; and (e) co-injection of the ThnG-catalyzed reaction with PS-5 (5) and the PS-7 sulfoxide diasteriomers (9) standard;

FIGS. 8a-8d show HPLC analysis (method 1) of the ThnG-catalyzed reaction with PS-7 (7). Ascending HPLC traces are offset by 30 s. (a) PS-7 (7) standard; (b) PS-7 sulfoxide diasteriomers (9) standard; (c) the ThnG-catalyzed reaction with PS-7 (7); and (d) co-injection of the ThnG-catalyzed reaction with PS-7 (7) and PS-7 sulfoxide diasteriomers (9);

FIGS. 9a-9e show HPLC (method 2) and ESI analysis of the reactions of ThnG with N-acetyl thienamycin (2) and ThnQ with PS7 (7): (a) PS-7 (7) standard; (b) N-acetyl thienamycin standard (2); (c) the ThnQ-catalyzed reaction with PS-7 (7). For N-acetyl dehydrothienamycin (3) $C_{13}H_{15}N_2O_5S$— theoretical (m/z 311.07) 9.90 min peak observed (m/z 311.13); (d) the ThnG-catalyzed reaction with N-acetyl thienamycin (2) N-acetyl dehydrotheinamycin (3) $C_{13}H_{15}N_2O_5S$— theoretical (m/z 311.07) 9.90 min peak observed (m/z 311.11); and (e) co-injection of the ThnG-catalyzed reaction with N-acetyl dehydrotheinamycin (3), and the ThnQ-catalyzed reaction with PS-7 (7); and FIGS. 10a-10j shows the synthesis of carbapenems. a. SmI$_2$, iPrOH, Sm(0), 81% b. CH$_2$Cl$_2$, TBSOTf, Et$_3$N, 92% c. THF, H$_2$, Pd/C, 99% d. 1. CH$_2$Cl$_2$, cat. DMF, oxalyl chloride 2. Et$_2$O, diazomethane, 99% e. THF, 2% H$_2$O, hv, 96% f 1. CH$_3$CN, carbonyl diimidazole 2. Mg(mono-PNB malonate)$_2$ 3. MeOH, 20% 1M HCl 4. CH$_3$CN, mesyl azide, Et$_3$N, 33% g. 1. benzene, Rh$_2$OAc$_4$, 80° C. 2. CH$_3$CN, cat. DMAP, diisopropylethyl amine, diphenyl chlorophosphate, 0° C. 3. DIEA, RSH, 43% h. 1. benzene, $Rh_2OAc_4$, 80° C. 2. THF/MeOH, $NaBH_4$, −78° C. 3. $CH_2Cl_2$, mesyl chloride, $Et_3N$, 49% 1. DMF, $Et_3N$, N-acetyl cysteamine, 30% (each diastereomer) j. $H_2O$, m-CPBA, 0° C., 99%.

DETAILED DESCRIPTION

The presently disclosed subject matter now will be described more fully hereinafter with reference to the accompanying Figures, in which some, but not all embodiments of the presently disclosed subject matter are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Figures. Therefore, it is to be understood that the presently disclosed subject matter is not to be limited to the specific embodiments disclosed and that modifications and other embodiments are intended to be included within the scope of the appended claims.

I. Method for Late Introduction of the (8R)-Hydroxyl Group in Carbapenem β-Lactam Antibiotic Synthesis Carbapenems are a class of β-lactam antibiotics with a broad spectrum of antibacterial activity. The general structure of carbapenems is provided immediately herein below:

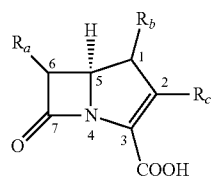

A common structural feature of some carbapenem antibiotics is the (8R)-hydroxyl group (i.e., a 1-hydroxyl-ethyl moiety) at the C-6 position. Currently-used synthetic methods introduce what will become the (8R)-hydroxyl group in the final product early in the synthetic process. This group must be protected, conserved and ultimately deprotected to the commercially useful carbapenem β-lactam antibiotic. The presently disclosed subject matter provides a simpler, more robust synthesis of this class of compounds.

In particular embodiments, the presently disclosed subject matter provides a method for preparing a carbapenem, wherein the method comprises an isolated, cloned, and overproduced enzyme that regio- and stereospecifically introduces an (8R)-hydroxyl group into a carbapenem bearing a simple C-6 ethyl group. Regio- and stereospecific introduction of the (8R)-hydroxyl group to clinically-used carbapenem β-lactam antibiotics late in a chemoenzymatic production process allows the use of simpler, more chemically robust starting materials from the outset, which allows more vigorous reaction conditions in subsequent steps. Further, the presently disclosed enzyme exhibits high stereospecificity and substrate selectivity. As a result, a racemic substrate, i.e., a starting material, is both resolved by differential reaction and the desired enantiomer is hydroxylated. That is, one enantiomer will react and the other will not react, or will react at a vastly slower rate, so that an optically-pure hydroxylated product will result.

Further, the presently disclosed enzyme displays flexibility as to the nature of the C-2 substituent. Typically, the C-2 substituent is a thioether derived from cysteamine (e.g. N-acetylcysteamine, or formamidino), S-pantethienyl or from 4-mercaptoproline. One of ordinary skill in the art upon review of the presently disclosed subject matter would recognize that other C-2 substituents are suitable for use with the presently disclosed methods. Accordingly, the presently disclosed subject matter provides a more efficient and less expensive chemoenzymatic route to these increasingly important antibiotics capable of overcoming resistance mechanisms redesigning existing synthetic routes and introduction of the (8R)-hydroxyl group in a late step.

Accordingly, in some embodiments, the presently disclosed subject matter provides a process for preparing a carbapenem of Formula (I):

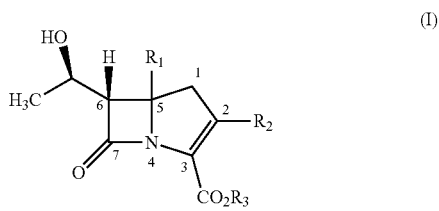

the process comprising contacting or incubating a carbapenem substrate of Formula (Ia):

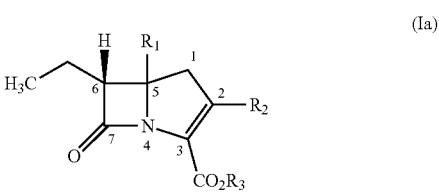

with a ThnQ enzyme under reaction conditions to produce the carbapenem of Formula (I); wherein: $R_1$ is H; $R_2$ is selected from the group consisting of —$SCH_2CH_2NH_2$, —SCH=CHNHC(=O)$CH_3$, —S-pantethienyl, —$SCH_2CH_2$NHC(=O)R', wherein R' is $C_1$-$C_{10}$ substituted or unsubstituted linear or branched alkyl, which can be further substituted with one or more 3-6 member cycloalkyl rings, or aminoalkyl, e.g., aminopropryl; wherein, in some embodiments, —C(=O)R' is selected from the group consisting of glycyl, beta-alanyl, 2-hydroxyacetyl, 2-methoxyacetyl, 3-hydroxypropionyl, 4-hydroxybutanoyl, and 3,4-dihydroxybutanoyl; and $R_3$ is H.

In some embodiments, the compound of Formula (I) is selected from the group consisting of:

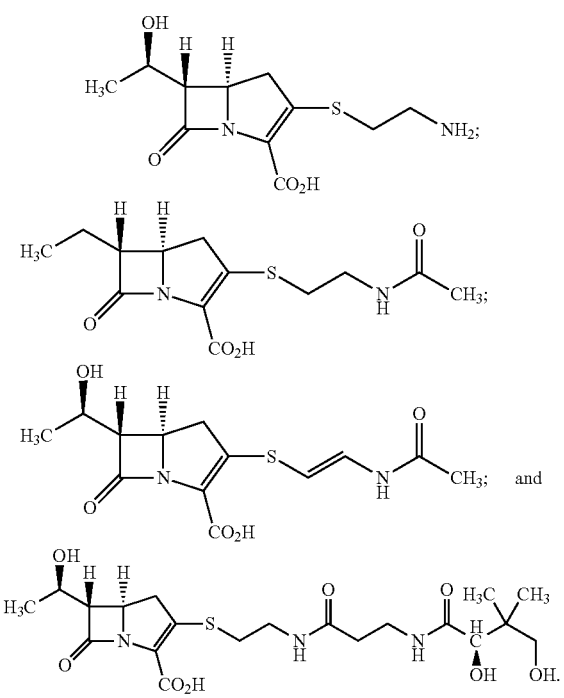

In other embodiments, the presently disclosed subject matter provides a process for preparing a carbapenem of Formula (II):

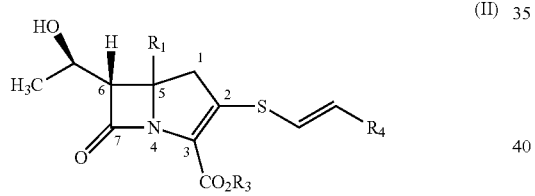

the process comprising contacting or incubating a carbapenem substrate of Formula (IIa):

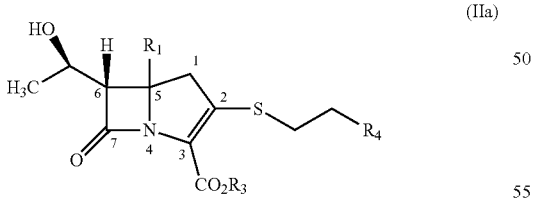

with a ThnG enzyme under reaction conditions to produce the carbapenem of Formula (II); wherein: $R_1$ is H; $R_2$ is selected from the group consisting of, —NH-glycyl, —NH-beta-alanyl, —NHC(=O)CH$_2$CH$_2$CH$_2$NH$_2$, —NH-pantethenic acid amide, acyl groups comprising $C_1$-$C_{10}$ substituted and unsubstituted linear and branched alkyl, which in some embodiments can further comprise one or more 3-6 member cycloalkyl rings, 2-hydroxyacetyl, 2-methoxyacetyl, 3-hydroxypropionyl, 4-hydroxybutanoyl, 3,4-dihydroxybutanoyl; and $R_3$ is H.

In some embodiments, the carbapenem of Formula (II) is:

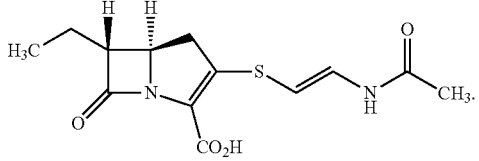 [SMILES: CC[C@H]1C(=O)N2C(C(=O)O)=C(S/C=C/NC(C)=O)C[C@H]12]

In yet other embodiments, the presently disclosed subject matter provides a process for preparing a carbapenem of Formula (III):

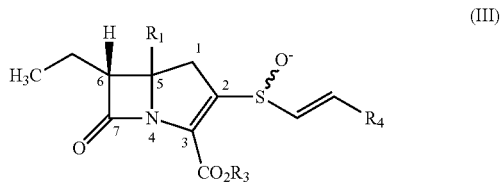

the process comprising contacting or incubating a carbapenem substrate of Formula (IIIa):

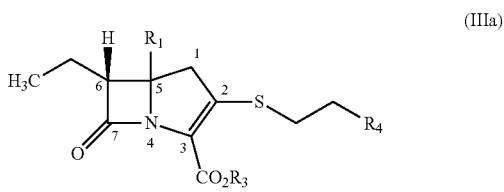

with a ThnG enzyme under reaction conditions to produce a carbapenem of Formula (IIIb):

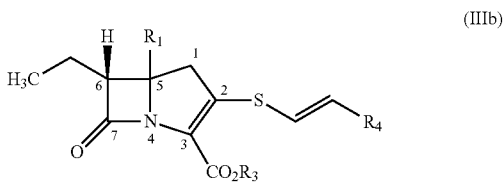

then contacting or incubating the carbapenem of Formula (IIIb) with a ThnG enzyme under reaction conditions to produce a carbapenem of Formula (III); wherein: $R_1$ is H; $R_2$ is selected from the group consisting of —NH-glycyl, —NH-beta-alanyl, —NHC(=O)CH$_2$CH$_2$CH$_2$NH$_2$, —NH-pantethenic acid amide, acyl groups comprising $C_1$-$C_{10}$ substituted and unsubstituted linear and branched alkyl, which in some embodiments can further comprise one or more 3-6 member cycloalkyl rings, 2-hydroxyacetyl, 2-methoxyacetyl, 3-hydroxypropionyl, 4-hydroxybutanoyl, 3,4-dihydroxybutanoyl; and $R_3$ is H.

In some embodiments, the carbapenem of Formula (III) is:

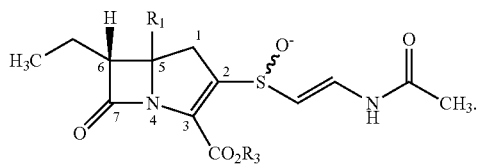

The terms "thnQ enzyme" and "thnG enzyme" refer to enzymes encoded by the naturally occurring or wild-type nucleotide sequence, as shown in SEQ ID NO: 5 and SEQ ID NO: 6, respectively, as well as the naturally occurring or wild-type amino acid sequence, as shown in SEQ ID NO: 7 and SEQ ID NO: 8, respectively. The terms also refer to enzymes with the same or similar function, but which differ in nucleotide and/or amino acid sequences. Such isoforms can exist by multiple mechanisms including, but not limited to different gene loci, multiple alleles, different subunit interaction, different splice forms, or different post-translational modifications. Accordingly, the terms "thnQ enzyme" and "thnG enzyme" refer to mutants or variants thereof with substantial sequence identity to the wild-type forms. In particular embodiments, the present invention provides a thnQ enzyme and a thnG enzyme comprising a nucleotide sequence set forth in SEQ ID NO: 5 and SEQ ID NO: 6, respectively. The nucleotide sequence encoding a thnQ enzyme or a thnG enzyme also can be a nucleotide sequence that encodes a polypeptide comprising the amino acid sequence of SEQ ID NO: 7 and SEQ ID NO: 8, respectively. In further embodiments, the nucleotide sequence encoding a thnQ enzyme or a thnG enzyme may comprise a nucleotide sequence that encodes polypeptides comprising an amino acid sequence having at least about 90% sequence identity to the amino acid sequence of SEQ ID NO:7 and SEQ ID NO:8, respectively.

The term "sequence identity" means that two polynucleotide sequences are identical (i.e., on a nucleotide-by-nucleotide basis) over the window of comparison. The term "percentage of sequence identity" means that two polynucleotide sequences are identical (i.e., on a nucleotide-by-nucleotide basis) over the window of comparison. The term "percentage of sequence identity" can be calculated, for example, by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity," "substantial sequence identity" and "substantially identical to", as used herein, denote a characteristic of a polynucleotide sequence, wherein the polynucleotide comprises a sequence that has at least about 80 percent sequence identity, at least about 85 sequence identity, at least about 90 percent sequence identity, at least about 95 percent sequence identity, at least about 96 percent sequence identity, at least about 97 percent sequence identity, at least about 98 percent sequence identity, or at least about 99 percent sequence identity as compared to a reference polynucleotide sequence over a comparison window of at least 20 nucleotide positions. As applied to polypeptides, the term "substantial identity," "substantial sequence identity" and "substantially identical to," as used herein, means that two polypeptide sequences, when optimally aligned, such as by the programs GAP or BESTFIT using default gap weights, share at least about 80 percent sequence identity, at least about 85 sequence identity, at least about 90 percent sequence identity, at least about 95 percent sequence identity, at least about 96 percent sequence identity, at least about 97 percent sequence identity, at least about 98 percent sequence identity, or at least about 99 percent sequence identity to a reference polypeptide sequence.

B. Non-Heme Iron Oxygenases Generate Natural Structural Diversity in Carbapenem Antibiotics Carbapenem antibiotics are of clinical importance because of their high potency, broad spectrum of antimicrobial activity, and resistance to most β-lactamases. Bonfiglio, G., et al., *Expert Opin. Invest. Drugs* 11(4):529-544 (2002). Thienamycin (1) (FIG. 1), the most potent natural member of this family, co-occurs in *Streptomyces cattleya* with four carbapenems that are distinguished by their C-2/C-6 substituents. Wilson, K. E., et al., *J. Antibiot.* 36(9):1109-1117 (1983). More than 50 carbapenam/em metabolites are known, many of which are differentiated only by the oxidation state of their C-2/C-6 substituents. The C-6 ethyl side chain of 1 is derived by $C_1$-donations from methionine, Houck, D. R., et al., *J. Am. Chem. Soc.* 108(17):5365-5366 (1986); Williamson, J. M., et al., *J. Biol. Chem.* 260(8):4637-4647 (1985), and can be methyl, ethyl, or isopropyl, which can be saturated, unsaturated, hydroxylated, or sulfated. Recent work has established that coenzyme A is successively truncated by three enzymes encoded by the thienamycin gene cluster to give the C-2 cysteamine moiety. Freeman, M. F., et al., *Proc. Natl. Acad. Sci. U.S.A.* 105(32):11128-11133 (2008).

This side chain can be pantetheine, but is generally cysteamine, which can be

N-acetylated or N-propionylated, desaturated and further oxidized to the sulfoxide, or cleaved and oxidized in a stepwise fashion to the sulfonic acid. These carbapenem metabolites comprise a natural combinatorial library whose structural modifications temper the high intrinsic hydrolytic instability of the carbapenem nucleus, as well as affect the antimicrobial spectrum and β-lactamase resistance of each family member. Bonfiglio, G., et al., *Expert Opin. Invest. Drugs* 11(4):529-544 (2002). Some of the higher oxidation state carbapenems have either enhanced antibiotic activity or increased β-lactamase resistance, and so, in the broad context of carbapenem biosynthesis, the origin of this oxidative diversity is of particular interest.

The variability of the carbapenem side chain oxidation state, as well as the discovery of a mutant strain, Rosi, D., et al., *J. Antibiot.* 34(3):341-343 (1981), of *Streptomyces cattleya* that produced deshydroxy thienamycin (10) instead of thienamycin (1) suggested that the thienamycin gene cluster, Nunez, L. E., et al., *Chem. Biol.* 10(4):301-311 (2003), encoded one or more enzyme(s) capable of oxidizing the C-2/C-6 moieties of carbapenems. Protein sequence analysis of ThnG and ThnQ indicated that each enzyme contained the $Hx(D/E)x_nH$ motif characteristic of nonheme Fe(II)/α-ketoglutarate (α-KG)-dependent dioxygenases. Hausinger, R. P. *Crit. Rev. Biochem. Mol.* 39:(1):21-68 (2004).

ThnG and ThnQ, however, are in the same family as CarC encoded by the (5R)-carbapenem-3-carboxylate (13) gene cluster in *Pectobacterium carotovorum*. McGowan, S. J., et al., *Mol. Microbiol.* 22(3):415-426 (1996); Li, R. F., et al., *J. Am. Chem. Soc.* 122(38):9296-9297 (2000). Despite low homology to CarC, ThnG and ThnQ have been postulated to catalyze steps in thienamycin biosynthesis analogous to the coupled C-5 epimerization and C-2/C-3 desaturation of (2S, 5S)-carbapenam (11) to (5R)-carbapenem-3-carboxylate (13) catalyzed by CarC. Hamed, R. B., et al., *ChemBioChem*

10(2):246-250 (2009). To discern their roles in thienamycin biosynthesis, ThnG and ThnQ were analyzed for carbapenem-oxidizing activity, as well as for the ability to catalyze C-5 epimerization and coupled or uncoupled C-2/C-3 desaturation of carbapenams/ems.

The analysis required carbapenam/ems varying in stereochemical configuration at C-6, as well as C-2/C-6 oxidation state/substitution pattern to serve as substrates and reference standards. Two methods were employed to establish the C-6 substituent and C-5/C-6 configuration by synthesizing precursor azetidinones. The first method provided the trans (3S, 4R)-configuration by alkylating the enolate of an azetidinone derived from L-aspartic acid. Reider, P. J. and Grabowski, E. J. J. *Tetrahedron Lett.* 23(22):2293-2296 (1982). The second method employed a catalytic asymmetric azetidinone-forming reaction that produced either enantiomer of the cis 3,4-disubstituted azetidinones with independent control of the carbapenem C-8 stereocenter. Bodner, M. J., et al., *Org. Lett.* 11(16):3606-3609 (2009).

These compounds could be used as precursors of cis or trans carbapenems. Azetidinones were converted to carbapenems by the Merck method, which allowed various C-2 groups to be introduced. Salzmann, T. N., et al., *J. Am. Chem. Soc.* 102(19):6161-6163 (1980); Ueda, Y., et al., *Can. J. Chem.* 62(12):2936-2940 (1984). The intermediate 2-oxocarbapenems in this route can be reduced and directed to the preparation of carbapenams bearing thioether substituents at C-2 (FIG. 1c). Freeman, M. F., et al., *Proc. Natl. Acad. Sci. U.S.A.* 105(32):11128-11133 (2008).

Carbapenam thioethers 14-17, (2S,5S)-carbapenam (11), (2S,5R)-carbapenam (12), Stapon, A., et al., *J. Am. Chem. Soc.* 2003, 125 (51):15746-15747 (2003), and 5-epi-PS-5 (6) were synthesized to test ThnG and ThnQ for coupled or uncoupled carbapenam ring epimerization and desaturation. PS-5 (5) was synthesized to test for side chain oxidation activity, because the acetylated cysteaminyl side chain is more stable than the unacetylated deshydroxy thienamycin (10). PS-7 (7), PS-7 sulfoxide (9), PS-5 sulfoxide (8), N-acetyl thienamycin (2), and the diastereomeric mixture (8S,R)-N-acetyl thienamycin (4) were synthesized as additional substrates and reference standards.

Figure 2:
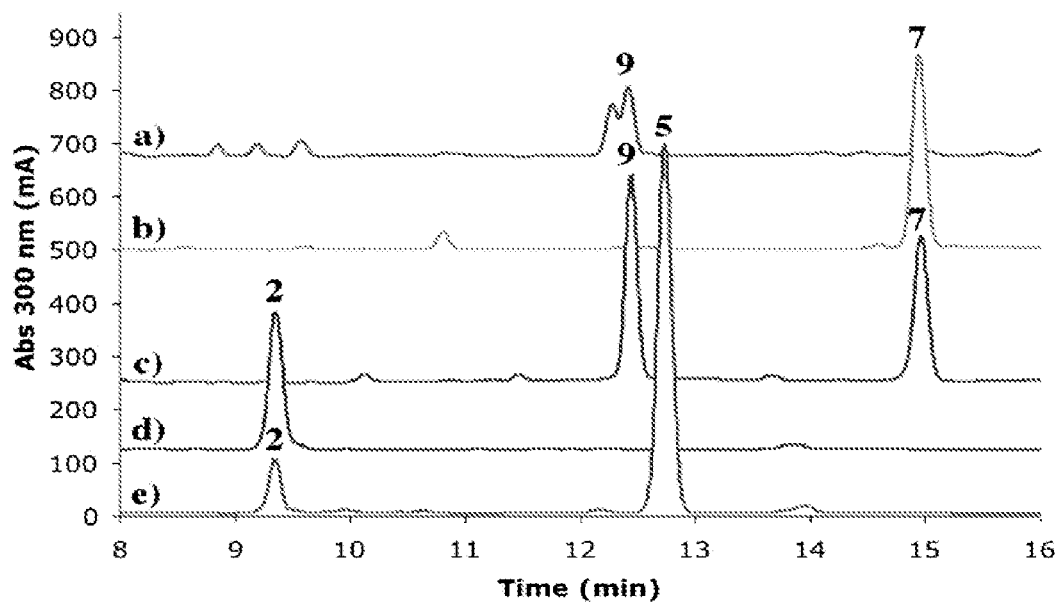
Figure 3:
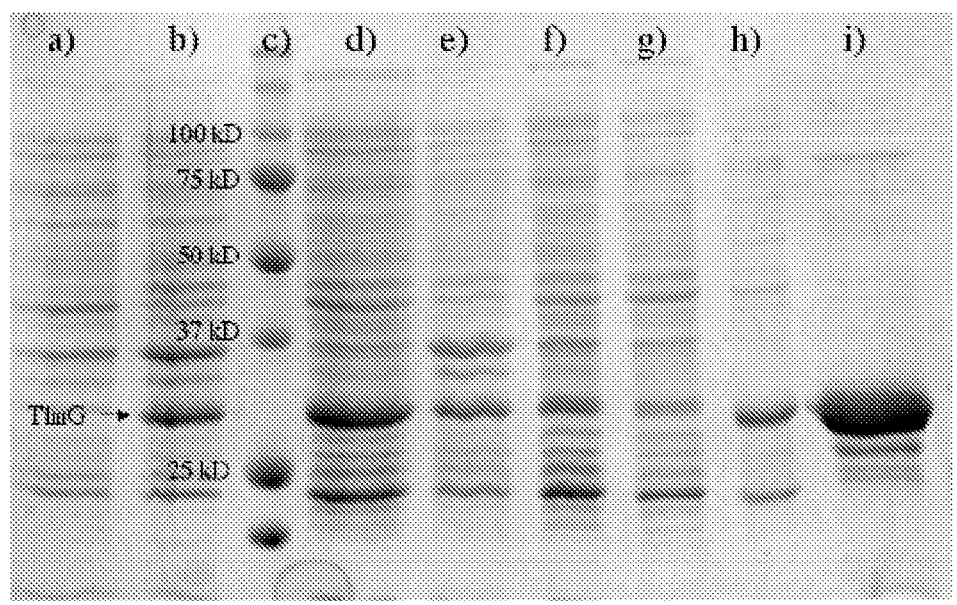
Figure 4:
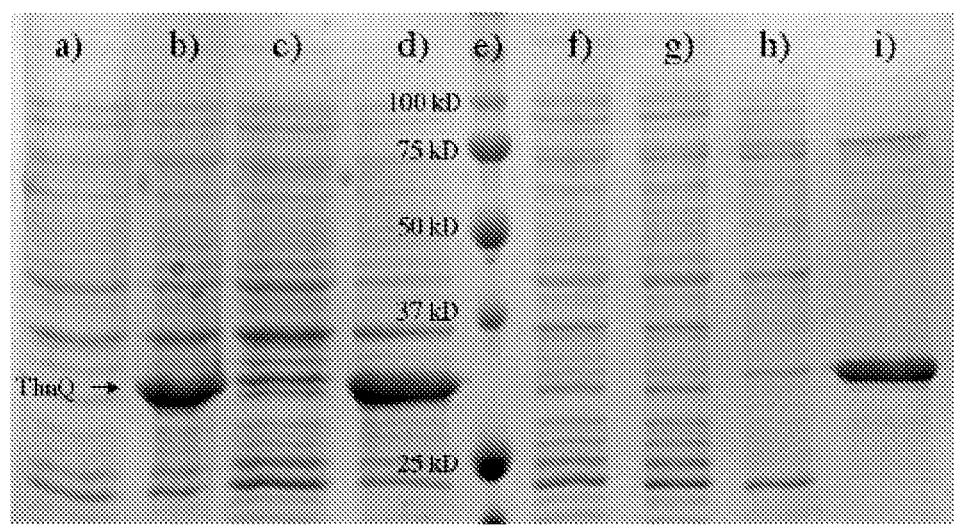
Figure 5:
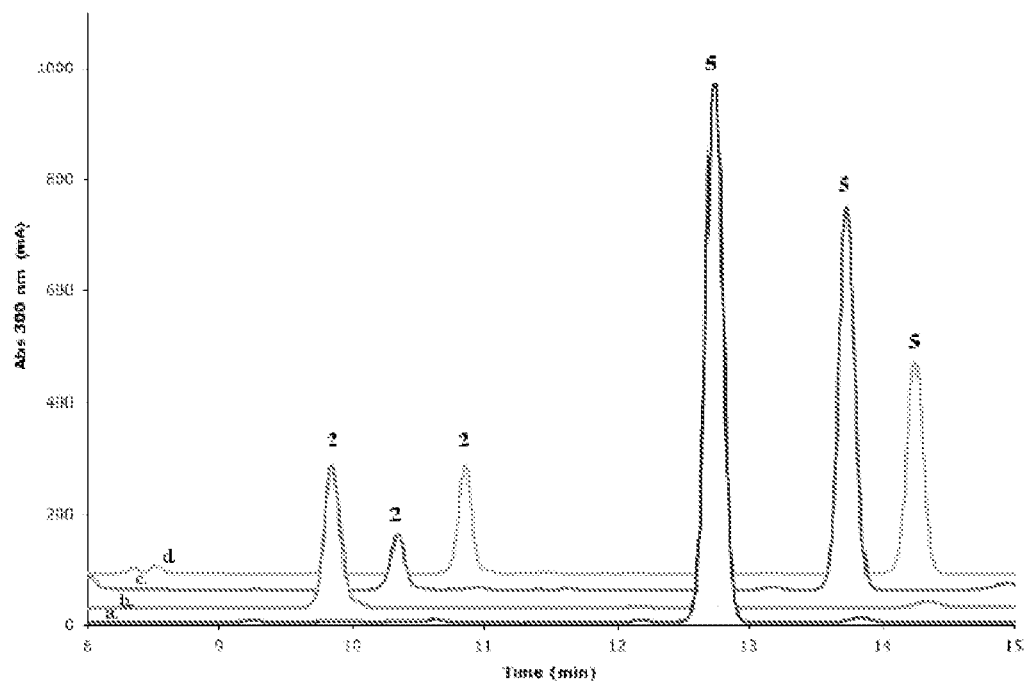

Thienamycin biosynthetic cluster genes thnG and thnQ were cloned from genomic DNA and inserted into pET29b each bearing a C-terminal His$_6$-tag. The recombinant proteins were overproduced in *E. coli* Rosetta2(DE3) and purified by Ni-NTA affinity chromatography. In vitro reactions in MOPS, pH 7.0, containing Fe(NH$_4$)$_2$(SO$_4$)$_2$, α-KG, ascorbate, the subject carbapenam/em, and either ThnG or ThnQ were incubated and analyzed by HPLC for the formation of new product(s). Salowe, S. P., et al., *Biochemistry* 29(27): 6499-6508 (1990); Decristoforo, G. *Anal. Chim. Acta* 163 (SEP):25-33 (1984). Clear outcomes were observed for both ThnG- and ThnQ-catalyzed reactions with PS-5 (5) (FIG. 2). The products were immediately identifiable as carbapenems by their unique chromophores ($\lambda_{max}$=290-320 nm). ThnQ produced a single new product more polar than 5, while ThnG produced two products, one with a shorter retention time and one with a longer retention time than that of 5.

Figure 6:
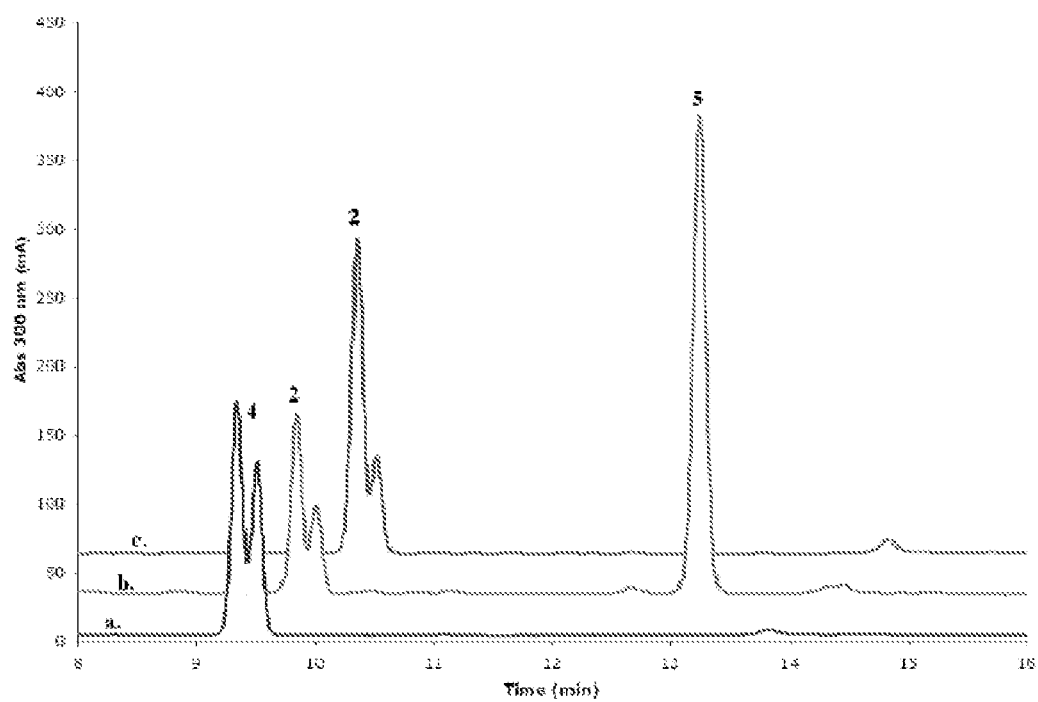
Figure 7:
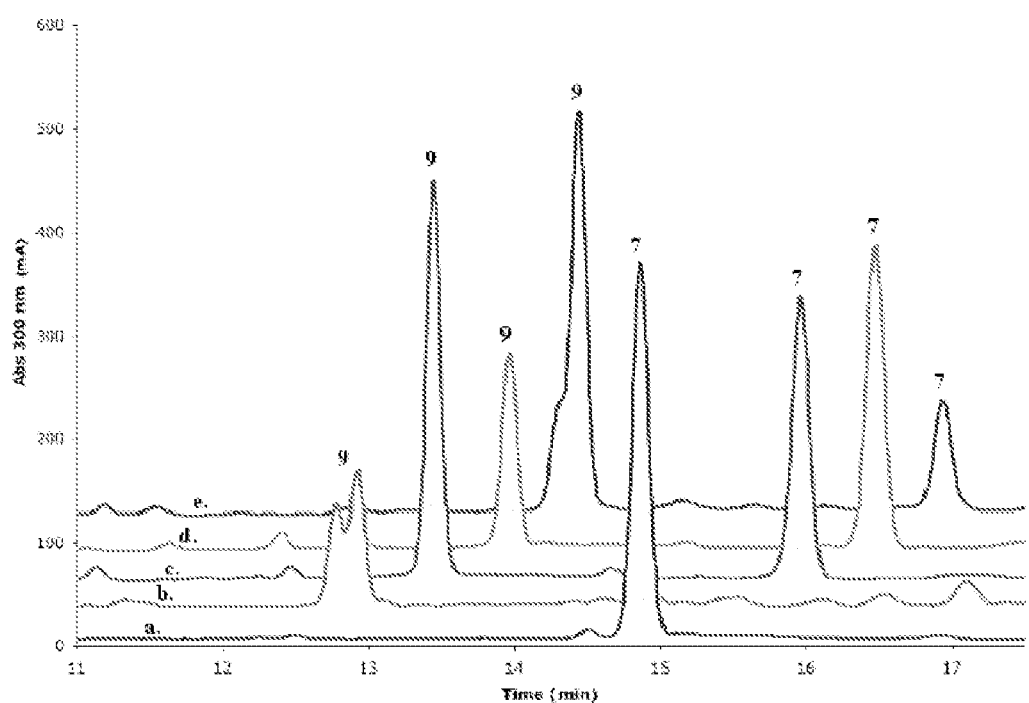

ESI mass spectrometric analysis of the new product (m/z=313.05) in the ThnQ-catalyzed reaction established that a single oxygen had been incorporated. Its identity was determined by co-injection with N-acetyl thienamycin (2) and (8S,R)-N-acetyl thienamycin (4) (FIGS. 2d,e, 5). This HPLC comparison demonstrated that ThnQ stereospecifically hydroxylated PS-5 (5) to produce 2. The chromatographically distinct (8S)-N-acetyl thienamycin diastereomer was not detected (FIG. 6).

Figure 8:
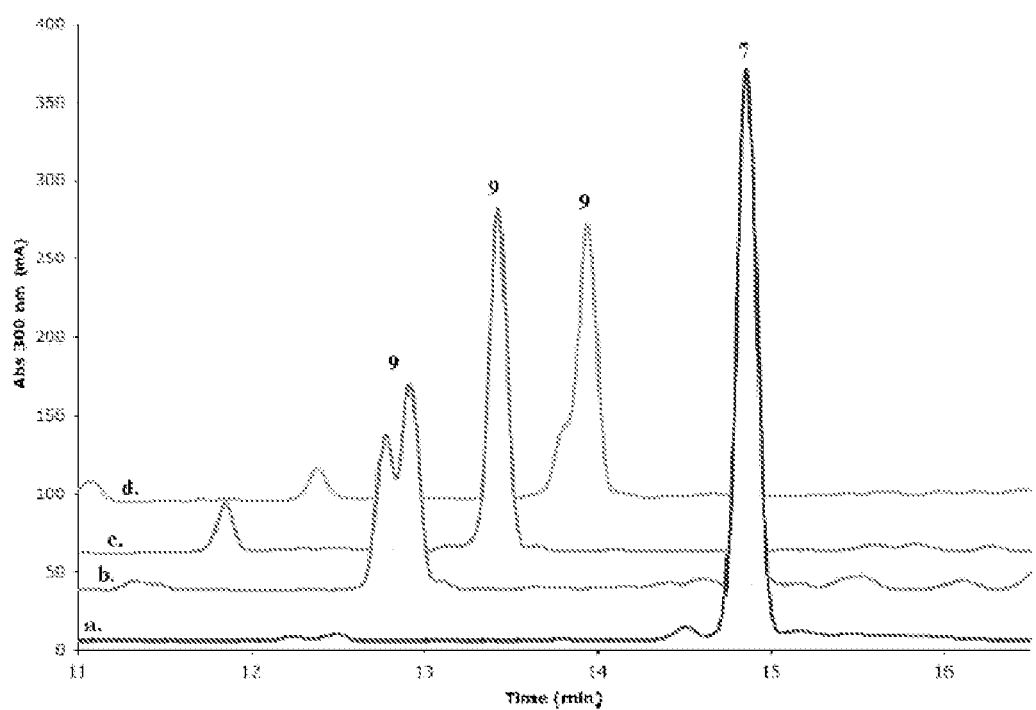
Figure 9:
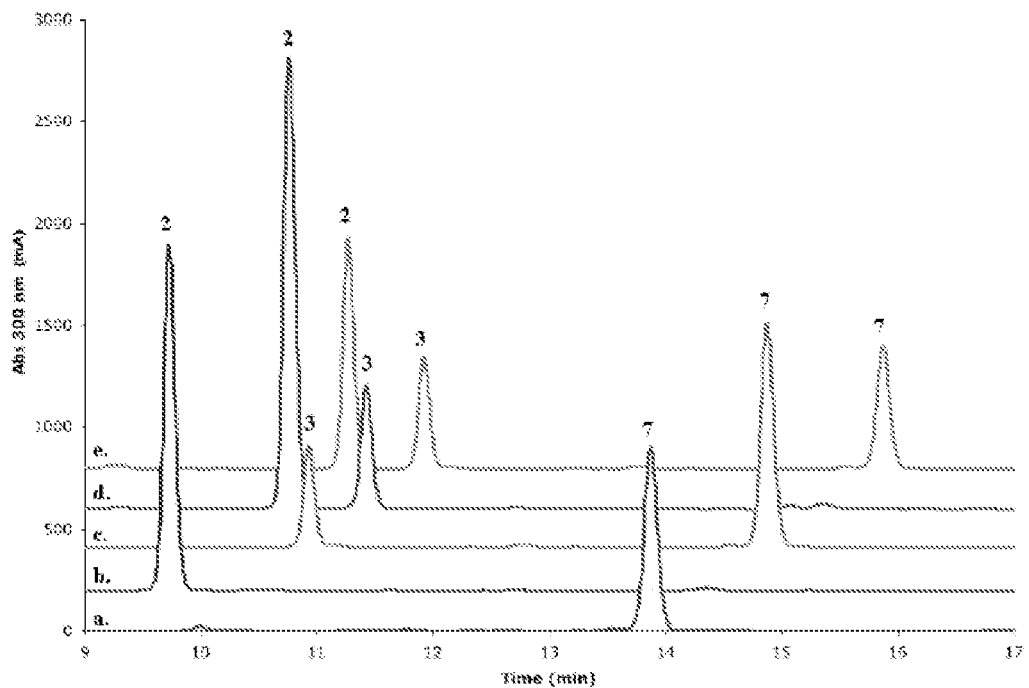
Figure 10:
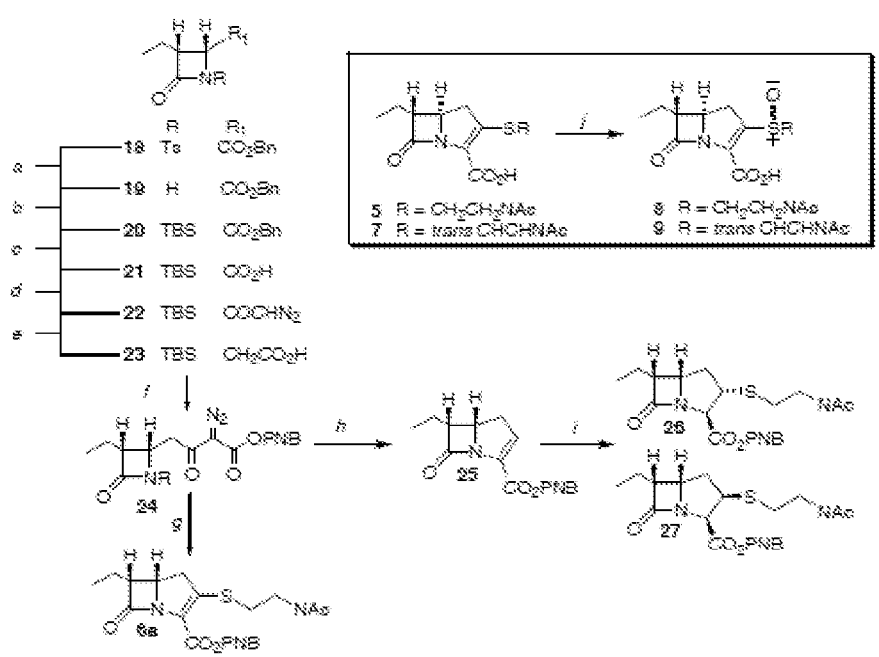

ESI-MS analysis of the products of the ThnG-catalyzed reaction with 5 indicated that the late eluting product (m/z=295.05) had an additional degree of unsaturation relative to 5 and the early eluting product (m/z=311.15) was both desaturated and oxidized. The carbapenems were identified as PS-7 (7) and PS-7 sulfoxide 9 by HPLC comparison to synthetic standards (FIGS. 2a-c, 7). ThnG also was able to convert 7 to its sulfoxide, but unable to catalyze desaturation when given PS-5 sulfoxide 8, indicating that desaturation precedes sulfoxidation (FIG. 8).

The oxidative relationships among carbapenems were further demonstrated by conversion of PS-7 (7) and N-acetyl thienamycin (2) into the *S. cattleya* metabolite N-acetyl dehydrothienamycin (3). Upon reaction with 2, ThnG produced a less polar product and ESI-MS indicated it contained an additional degree of unsaturation. ThnQ produced a more polar product on reaction with 7. These new products coeluted under HPLC, had identical masses by ESI-MS, and were assigned the same structure, N-acetyl dehydrothienamycin (3). Notably, no sulfoxide product was observed, consistent with the metabolite profile in *S. cattleya* and suggesting that ThnQ reaction precedes that of ThnG.

HPLC analyses of other carbapenam/ems (6, 11, 12, 14-17) tested with ThnG and ThnQ did not show appearance of a carbapenem chromophore or other new products. Additionally, in vitro reactions with carbapenam/ems (6, 11, 12, 14-17) employing cell-free extracts harboring ThnG or ThnQ were analyzed with the supersensitive *E. coli* SC 12155 and the Nitrocefin β-lactamase induction assay using *Bacillus licheniformis* ATCC 14580. Sykes, R. B. and Wells, J. S. *J. Antibiot.* 38(1):119-121 (1985); Gerratana, B., et al., *Biochemistry* 42 (25):7836-7847 (2003). No antibiotic production could be detected by these three sensitive measures.

The presently disclosed subject matter demonstrates that the Fe(II)/α-KG-dependent oxygenases ThnG and ThnQ oxidize the C-2 and C-6 side chains, respectively, of carbapenem substrates. No evidence was found that they catalyze coupled or uncoupled C-5 epimerization and/or C-2/C-3 desaturation in the carbapenam/ems tested. On these bases, it appears that the latter two reactions rely on other proteins encoded by the thienamycin gene cluster that are distinct from the non-heme iron oxygenases like CarC, key to the biosynthesis of (5R)-carbpenem-3-carboxylate (13). Li, R. F., et al., *J. Am. Chem. Soc.* 122(38):9296-9297 (2000); Hamed, R. B., et al., *ChemBioChem* 10(2):246-250 (2009); Stapon, A., et al., *J. Am. Chem. Soc.* 125(28):8486-8493 (2003).

Oxidative modifications of the C-2 and C-6 side chains of carbapenems are major determinants of their antimicrobial spectrum and β-lactamase resistance. These activities strongly suggest that the known carbapenems produced by *S. cattleya* arise from ThnG and ThnQ oxidation of a common biosynthetic precursor and that much of the structural diversity exemplified by this class of antibiotics likely derives from orthologues present in other carbapenem producers. Knowledge of these oxidative relationships will more sharply refine further biosynthetic investigations of this antibiotic family.

C. Chemical Definitions

While the following terms in relation to compounds of Formulae (I-III) are believed to be well understood by one of ordinary skill in the art, the following definitions are set forth to facilitate explanation of the presently disclosed subject matter. These definitions are intended to supplement and illustrate, not preclude, the definitions that would be apparent to one of ordinary skill in the art upon review of the present disclosure.

The terms substituted, whether preceded by the term "optionally" or not, and substituent, as used herein, refer to the ability, as appreciated by one skilled in this art, to change one functional group for another functional group provided that the valency of all atoms is maintained. When more than one position in any given structure may be substituted with more than one substituent selected from a specified group, the substituent may be either the same or different at every position. The substituents also may be further substituted (e.g., an aryl group substituent may have another substituent off it, such as another aryl group, which is further substituted, for example, with fluorine at one or more positions).

Where substituent groups or linking groups are specified by their conventional chemical formulae, written from left to right, they equally encompass the chemically identical substituents that would result from writing the structure from right to left, e.g., —CH$_2$O— is equivalent to —OCH$_2$—; —C(=O)O— is equivalent to —OC(=O)—; —OC(=O)NR— is equivalent to —NRC(=O)O—, and the like.

When the term "independently selected" is used, the substituents being referred to (e.g., R groups, such as groups $R_1$, $R_2$, and the like, or variables, such as "m" and "n"), can be identical or different. For example, both $R_1$ and $R_2$ can be substituted alkyls, or $R_1$ can be hydrogen and $R_2$ can be a substituted alkyl, and the like.

The terms "a," "an," or "a(n)," when used in reference to a group of substituents herein, mean at least one. For example, where a compound is substituted with "an" alkyl or aryl, the compound is optionally substituted with at least one alkyl and/or at least one aryl. Moreover, where a moiety is substituted with an R substituent, the group may be referred to as "R-substituted." Where a moiety is R-substituted, the moiety is substituted with at least one R substituent and each R substituent is optionally different.

A named "R" or group will generally have the structure that is recognized in the art as corresponding to a group having that name, unless specified otherwise herein. For the purposes of illustration, certain representative "R" groups as set forth above are defined below.

Descriptions of compounds of the present disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The term hydrocarbon, as used herein, refers to any chemical group comprising hydrogen and carbon. The hydrocarbon may be substituted or unsubstituted. As would be known to one skilled in this art, all valencies must be satisfied in making any substitutions. The hydrocarbon may be unsaturated, saturated, branched, unbranched, cyclic, polycyclic, or heterocyclic. Illustrative hydrocarbons are further defined herein below and include, for example, methyl, ethyl, n-propyl, isopropyl, cyclopropyl, allyl, vinyl, n-butyl, tert-butyl, ethynyl, cyclohexyl, methoxyl, diethylamino, and the like.

The term "alkyl," by itself or as part of another substituent, means, unless otherwise stated, a straight (i.e., unbranched) or branched chain, acyclic or cyclic hydrocarbon group, or combination thereof, which may be fully saturated, mono- or polyunsaturated and can include di- and multivalent groups, having the number of carbon atoms designated (i.e., $C_1$-$C_{10}$ means one to ten carbons). In particular embodiments, the term "alkyl" refers to $C_{1-20}$ inclusive, linear (i.e., "straight-chain"), branched, or cyclic, saturated or at least partially and in some cases fully unsaturated (i.e., alkenyl and alkynyl) hydrocarbon radicals derived from a hydrocarbon moiety containing between one and twenty carbon atoms by removal of a single hydrogen atom.

Representative saturated hydrocarbon groups include, but are not limited to, methyl, ethyl, n-propyl, isopropyl, n-butyl, isobutyl, sec-butyl, tert-butyl, n-pentyl, sec-pentyl, iso-pentyl, neopentyl, n-hexyl, sec-hexyl, n-heptyl, n-octyl, n-decyl, n-undecyl, dodecyl, cyclohexyl, (cyclohexyl)methyl, cyclopropylmethyl, and homologs and isomers thereof. "Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to $C_{1-8}$ straight-chain alkyls. In other embodiments, "alkyl" refers, in particular, to $C_{1-8}$ branched-chain alkyls.

Alkyl groups can optionally be substituted (a "substituted alkyl") with one or more alkyl group substituents, which can be the same or different. The term "alkyl group substituent" includes but is not limited to alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl. There can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

The term "heteroalkyl," by itself or in combination with another term, means, unless otherwise stated, a stable straight or branched chain, or cyclic hydrocarbon group, or combinations thereof, consisting of at least one carbon atoms and at least one heteroatom selected from the group consisting of O, N, P, Si and S, and wherein the nitrogen, phosphorus, and sulfur atoms may optionally be oxidized and the nitrogen heteroatom may optionally be quaternized. The heteroatom(s) O, N, P and S and Si may be placed at any interior position of the heteroalkyl group or at the position at which alkyl group is attached to the remainder of the molecule. Examples include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_{25}$—S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, —CH=CH—N(CH$_3$)—CH$_3$, —O—CH$_3$, —O—CH$_2$—CH$_3$, and —CN. Up to two or three heteroatoms may be consecutive, such as, for example, —CH$_2$—NH—OCH$_3$ and —CH$_2$—O—Si(CH$_3$)$_3$.

As described above, heteroalkyl groups, as used herein, include those groups that are attached to the remainder of the molecule through a heteroatom, such as —C(O)R', —C(O)NR', —NR'R", —OR', —SR, and/or —SO$_2$R'. Where "heteroalkyl" is recited, followed by recitations of specific heteroalkyl groups, such as —NR'R or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

"Cyclic" and "cycloalkyl" refer to a non-aromatic mono- or multicyclic ring system of about 3 to about 10 carbon atoms, e.g., 3, 4, 5, 6, 7, 8, 9, or 10 carbon atoms. The cycloalkyl group can be optionally partially unsaturated. The cycloalkyl group also can be optionally substituted with an alkyl group substituent as defined herein, oxo, and/or alkylene. There can be optionally inserted along the cyclic alkyl chain one or more oxygen, sulfur or substituted or unsubstituted nitrogen atoms, wherein the nitrogen substituent is hydrogen, alkyl, substituted alkyl, aryl, or substituted aryl, thus providing a heterocyclic group. Representative monocyclic cycloalkyl rings include cyclopentyl, cyclohexyl, and cycloheptyl. Multicyclic cycloalkyl rings include adamantyl, octahydronaphthyl, decalin, camphor, camphane, and noradamantyl, and fused ring systems, such as dihydro- and tetrahydronaphthalene, and the like.

The term "cycloalkylalkyl," as used herein, refers to a cycloalkyl group as defined hereinabove, which is attached to the parent molecular moiety through an alkyl group, also as defined above. Examples of cycloalkylalkyl groups include cyclopropylmethyl and cyclopentylethyl.

The terms "cycloheteroalkyl" or "heterocycloalkyl" refer to a non-aromatic ring system, unsaturated or partially unsaturated ring system, such as a 3- to 10-member substituted or unsubstituted cycloalkyl ring system, including one or more heteroatoms, which can be the same or different, and are selected from the group consisting of nitrogen (N), oxygen (O), sulfur (S), phosphorus (P), and silicon (Si), and optionally can include one or more double bonds.

The cycloheteroalkyl ring can be optionally fused to or otherwise attached to other cycloheteroalkyl rings and/or non-aromatic hydrocarbon rings. Heterocyclic rings include those having from one to three heteroatoms independently selected from oxygen, sulfur, and nitrogen, in which the nitrogen and sulfur heteroatoms may optionally be oxidized and the nitrogen heteroatom may optionally be quaternized. In certain embodiments, the term heterocylic refers to a non-aromatic 5-, 6-, or 7-membered ring or a polycyclic group wherein at least one ring atom is a heteroatom selected from O, S, and N (wherein the nitrogen and sulfur heteroatoms may be optionally oxidized), including, but not limited to, a bi- or tri-cyclic group, comprising fused six-membered rings having between one and three heteroatoms independently selected from the oxygen, sulfur, and nitrogen, wherein (i) each 5-membered ring has 0 to 2 double bonds, each 6-membered ring has 0 to 2 double bonds, and each 7-membered ring has 0 to 3 double bonds, (ii) the nitrogen and sulfur heteroatoms may be optionally oxidized, (iii) the nitrogen heteroatom may optionally be quaternized, and (iv) any of the above heterocyclic rings may be fused to an aryl or heteroaryl ring. Representative cycloheteroalkyl ring systems include, but are not limited to pyrrolidinyl, pyrrolinyl, imidazolidinyl, imidazolinyl, pyrazolidinyl, pyrazolinyl, piperidyl, piperazinyl, indolinyl, quinuclidinyl, morpholinyl, thiomorpholinyl, thiadiazinanyl, tetrahydrofuranyl, and the like.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like.

Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. The terms "cycloalkylene" and "heterocycloalkylene" refer to the divalent derivatives of cycloalkyl and heterocycloalkyl, respectively.

An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. Alkyl groups which are limited to hydrocarbon groups are termed "homoalkyl."

More particularly, the term "alkenyl" as used herein refers to a monovalent group derived from a $C_{1-20}$ inclusive straight or branched hydrocarbon moiety having at least one carbon-carbon double bond by the removal of a single hydrogen atom. Alkenyl groups include, for example, ethenyl (i.e., vinyl), propenyl, butenyl, 1-methyl-2-buten-1-yl, pentenyl, hexenyl, octenyl, and butadienyl.

The term "cycloalkenyl" as used herein refers to a cyclic hydrocarbon containing at least one carbon-carbon double bond. Examples of cycloalkenyl groups include cyclopropenyl, cyclobutenyl, cyclopentenyl, cyclopentadiene, cyclohexenyl, 1,3-cyclohexadiene, cycloheptenyl, cycloheptatrienyl, and cyclooctenyl.

The term "alkynyl" as used herein refers to a monovalent group derived from a straight or branched $C_{1-20}$ hydrocarbon of a designed number of carbon atoms containing at least one carbon-carbon triple bond. Examples of "alkynyl" include ethynyl, 2-propynyl (propargyl), 1-propynyl, pentynyl, hexynyl, heptynyl, and allenyl groups, and the like.

The term "alkylene" by itself or a part of another substituent refers to a straight or branched bivalent aliphatic hydrocarbon group derived from an alkyl group having from 1 to about 20 carbon atoms, e.g., 1, 2, 3, 4, 5, 6, 7, 8, 9, 10, 11, 12, 13, 14, 15, 16, 17, 18, 19, or 20 carbon atoms. The alkylene group can be straight, branched or cyclic. The alkylene group also can be optionally unsaturated and/or substituted with one or more "alkyl group substituents." There can be optionally inserted along the alkylene group one or more oxygen, sulfur or substituted or unsubstituted nitrogen atoms (also referred to herein as "alkylaminoalkyl"), wherein the nitrogen substituent is alkyl as previously described. Exemplary alkylene groups include methylene (—CH$_2$—); ethylene (—CH$_2$—CH$_2$—); propylene (—(CH$_2$)$_3$—); cyclohexylene (—C$_6$H$_{10}$—); —CH=CH—CH=CH—; —CH=CH—CH$_2$—; —CH$_2$CH$_2$CH$_2$CH$_2$—, —CH$_2$CH=CHCH$_2$—, —CH$_2$CsCCH$_2$—, —CH$_2$CH$_2$CH(CH$_2$CH$_2$CH$_3$)CH$_2$—, —(CH$_2$)$_q$—N(R)—(CH$_2$)$_r$—, wherein each of q and r is independently an integer from 0 to about 20, e.g., 0, 1, 2, 3, 4, 5, 6, 7, 8, 9, 10, 11, 12, 13, 14, 15, 16, 17, 18, 19, or 20, and R is hydrogen or lower alkyl; methylenedioxyl (—O—CH$_2$—O—); and ethylenedioxyl (—O—(CH$_2$)$_2$—O—). An alkylene group can have about 2 to about 3 carbon atoms and can further have 6-20 carbons. Typically, an alkyl (or alkylene) group will have from 1 to 24 carbon atoms, with those groups having 10 or fewer carbon atoms being some embodiments of the present disclosure. A "lower alkyl" or "lower alkylene" is a shorter chain alkyl or alkylene group, generally having eight or fewer carbon atoms.

The term "heteroalkylene" by itself or as part of another substituent means a divalent group derived from heteroalkyl, as exemplified, but not limited by, —CH₂—CH₂—S—CH₂—CH₂— and —CH₂—S—CH₂—CH₂—NH—CH₂—. For heteroalkylene groups, heteroatoms can also occupy either or both of the chain termini (e.g., alkyleneoxo, alkylenedioxo, alkyleneamino, alkylenediamino, and the like). Still further, for alkylene and heteroalkylene linking groups, no orientation of the linking group is implied by the direction in which the formula of the linking group is written. For example, the formula —C(O)OR'— represents both —C(O)OR'— and —R'OC(O)—.

The term "aryl" means, unless otherwise stated, an aromatic hydrocarbon substituent that can be a single ring or multiple rings (such as from 1 to 3 rings), which are fused together or linked covalently. The term "heteroaryl" refers to aryl groups (or rings) that contain from one to four heteroatoms (in each separate ring in the case of multiple rings) selected from N, O, and S, wherein the nitrogen and sulfur atoms are optionally oxidized, and the nitrogen atom(s) are optionally quaternized. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of above noted aryl and heteroaryl ring systems are selected from the group of acceptable substituents described below. The terms "arylene" and "heteroarylene" refer to the divalent forms of aryl and heteroaryl, respectively.

For brevity, the term "aryl" when used in combination with other terms (e.g., aryloxo, arylthioxo, arylalkyl) includes both aryl and heteroaryl rings as defined above. Thus, the terms "arylalkyl" and "heteroarylalkyl" are meant to include those groups in which an aryl or heteroaryl group is attached to an alkyl group (e.g., benzyl, phenethyl, pyridylmethyl, furylmethyl, and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like). The term "haloaryl," however, as used herein, is meant to cover only aryls substituted with one or more halogens.

Where a heteroalkyl, heterocycloalkyl, or heteroaryl includes a specific number of members (e.g. "3 to 7 membered"), the term "member" refers to a carbon or heteroatom.

Further, a structure represented generally by the formula:

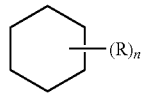

as used herein refers to a ring structure, for example, but not limited to a 3-carbon, a 4-carbon, a 5-carbon, a 6-carbon, a 7-carbon, and the like, aliphatic and/or aromatic cyclic compound, including a saturated ring structure, a partially saturated ring structure, and an unsaturated ring structure, comprising a substituent R group, wherein the R group can be present or absent, and when present, one or more R groups can each be substituted on one or more available carbon atoms of the ring structure. The presence or absence of the R group and number of R groups is determined by the value of the variable "n," which is an integer generally having a value ranging from 0 to the number of carbon atoms on the ring available for substitution. Each R group, if more than one, is substituted on an available carbon of the ring structure rather than on another R group. For example, the structure above where n is 0 to 2 would comprise compound groups including, but not limited to:

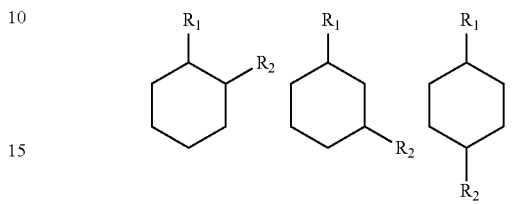

and the like.

A dashed line representing a bond in a cyclic ring structure indicates that the bond can be either present or absent in the ring. That is, a dashed line representing a bond in a cyclic ring structure indicates that the ring structure is selected from the group consisting of a saturated ring structure, a partially saturated ring structure, and an unsaturated ring structure. The symbol ( $\sim\!\!\sim\!\!\sim$ ) denotes the point of attachment of a moiety to the remainder of the molecule.

When a named atom of an aromatic ring or a heterocyclic aromatic ring is defined as being "absent," the named atom is replaced by a direct bond. Each of above terms (e.g., "alkyl," "heteroalkyl," "cycloalkyl, and "heterocycloalkyl", "aryl," "heteroaryl," "phosphonate," and "sulfonate" as well as their divalent derivatives) are meant to include both substituted and unsubstituted forms of the indicated group. Optional substituents for each type of group are provided below.

Substituents for alkyl, heteroalkyl, cycloalkyl, heterocycloalkyl monovalent and divalent derivative groups (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R'", —OC(O)R', —C(O)R', —CO₂R', —C(O)NR'R", —OC(O)NR'R", —NR"C(O)R', —NR'—C(O)NR"R'", —NR"C(O)OR', —NR—C(NR'R")=NR'", —S(O)R', —S(O)₂R', —S(O)₂NR'R", —NRSO₂R', —CN and —NO₂ in a number ranging from zero to (2m'+1), where m' is the total number of carbon atoms in such groups. R', R", R'" and R"" each may independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxyl or thioalkoxyl groups, or arylalkyl groups. As used herein, an "alkoxy" or "alkoxyl" group is an alkyl attached to the remainder of the molecule through a divalent oxygen. When a compound of the disclosure includes more than one R group, for example, each of the R groups is independently selected as are each R', R", R'" and R"" groups when more than one of these groups is present. When R' and R" are attached to the same nitrogen atom, they can be combined with the nitrogen atom to form a 4-, 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF₃ and —CH₂CF₃) and acyl (e.g., —C(O)CH₃, —C(O)CF₃, —C(O)CH₂OCH₃, and the like).

Similar to the substituents described for alkyl groups above, exemplary substituents for aryl and heteroaryl groups (as well as their divalent derivatives) are varied and are selected from, for example: halogen, —OR', —NR'R", —SR', -halogen, —SiR'R"R"', —OC(O)R', —C(O)R', —CO₂R', —C(O)NR'R", —OC(O)NR'R", —NR"C(O)R', —NR'—C(O)NR"R"', —NR"C(O)OR', —NR—C(NR'R"R"')=NR"", —NR—C(NR'R")=NR"'—S(O)R', —S(O)₂R', —S(O)₂NR'R", —NRSO₂R', —CN and —NO₂, —R', —N₃, —CH(Ph)₂, fluoro(C₁-C₄)alkoxo, and fluoro (C₁-C₄)alkyl, in a number ranging from zero to the total number of open valences on aromatic ring system; and where R', R", R"' and R"" may be independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. When a compound of the disclosure includes more than one R group, for example, each of the R groups is independently selected as are each R', R", R"' and R"" groups when more than one of these groups is present.

Two of the substituents on adjacent atoms of aryl or heteroaryl ring may optionally form a ring of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of aryl or heteroaryl ring may optionally be replaced with a substituent of the formula -A-(CH₂)$_r$—B—, wherein A and B are independently —CRR'—, —O—, —NR—, —S—, —S(O)—, —S(O)₂—, —S(O)₂NR'— or a single bond, and r is an integer of from 1 to 4.

One of the single bonds of the new ring so formed may optionally be replaced with a double bond. Alternatively, two of the substituents on adjacent atoms of aryl or heteroaryl ring may optionally be replaced with a substituent of the formula —(CRR')$_s$—X'—(C"R"')$_d$—, where s and d are independently integers of from 0 to 3, and X' is —O—, —NR'—, —S—, —S(O)—, —S(O)₂—, or —S(O)₂NR'—. The substituents R, R', R" and R"' may be independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the term "acyl" refers to an organic acid group wherein the —OH of the carboxyl group has been replaced with another substituent and has the general formula RC(=O)—, wherein R is an alkyl, alkenyl, alkynyl, aryl, carbocyclic, heterocyclic, or aromatic heterocyclic group as defined herein). As such, the term "acyl" specifically includes arylacyl groups, such as an acetylfuran and a phenacyl group. Specific examples of acyl groups include acetyl and benzoyl.

The term "glycyl" refers to an —C(=O)—CH₂NH₂ group; the term "β-alanyl" refers to an —C(=O)—CH(NH₂)—CH₃ group; and the term "pantethienyl" group refers to the following moiety, wherein the term "S-pantethienyl" denotes that the group is attached via a the sulfur atom:

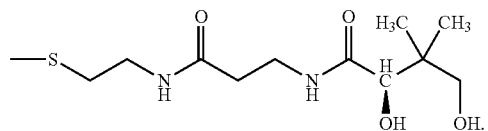

The terms "alkoxyl" or "alkoxy" are used interchangeably herein and refer to a saturated (i.e., alkyl-O—) or unsaturated (i.e., alkenyl-O— and alkynyl-O—) group attached to the parent molecular moiety through an oxygen atom, wherein the terms "alkyl," "alkenyl," and "alkynyl" are as previously described and can include C₁₋₂₀ inclusive, linear, branched, or cyclic, saturated or unsaturated oxo-hydrocarbon chains, including, for example, methoxyl, ethoxyl, propoxyl, isopropoxyl, n-butoxyl, sec-butoxyl, t-butoxyl, and n-pentoxyl, neopentoxyl, n-hexoxyl, and the like.

The term "alkoxyalkyl" as used herein refers to an alkyl-O-alkyl ether, for example, a methoxyethyl or an ethoxymethyl group.

"Aryloxyl" refers to an aryl-O— group wherein the aryl group is as previously described, including a substituted aryl. The term "aryloxyl" as used herein can refer to phenyloxyl or hexyloxyl, and alkyl, substituted alkyl, halo, or alkoxyl substituted phenyloxyl or hexyloxyl.

"Aralkyl" refers to an aryl-alkyl-group wherein aryl and alkyl are as previously described, and included substituted aryl and substituted alkyl. Exemplary aralkyl groups include benzyl, phenylethyl, and naphthylmethyl.

"Aralkyloxyl" refers to an aralkyl-O— group wherein the aralkyl group is as previously described. An exemplary aralkyloxyl group is benzyloxyl.

"Alkoxycarbonyl" refers to an alkyl-O—CO— group. Exemplary alkoxycarbonyl groups include methoxycarbonyl, ethoxycarbonyl, butyloxycarbonyl, and t-butyloxycarbonyl.

"Aryloxycarbonyl" refers to an aryl-O—CO— group. Exemplary aryloxycarbonyl groups include phenoxy- and naphthoxy-carbonyl.

"Aralkoxycarbonyl" refers to an aralkyl-O—CO— group. An exemplary aralkoxycarbonyl group is benzyloxycarbonyl.

"Carbamoyl" refers to an amide group of the formula —CONH₂. "Alkylcarbamoyl" refers to a R'RN—CO— group wherein one of R and R' is hydrogen and the other of R and R' is alkyl and/or substituted alkyl as previously described. "Dialkylcarbamoyl" refers to a R'RN—CO— group wherein each of R and R' is independently alkyl and/or substituted alkyl as previously described.

The term carbonyldioxyl, as used herein, refers to a carbonate group of the formula —O—CO—OR.

"Acyloxyl" refers to an acyl-O— group wherein acyl is as previously described.

The term "amino" refers to the —NH₂ group and also refers to a nitrogen containing group as is known in the art derived from ammonia by the replacement of one or more hydrogen radicals by organic radicals. For example, the terms "acylamino" and "alkylamino" refer to specific N-substituted organic radicals with acyl and alkyl substituent groups respectively.

An "aminoalkyl" as used herein refers to an amino group covalently bound to an alkylene linker. More particularly, the terms alkylamino, dialkylamino, and trialkylamino as used herein refer to one, two, or three, respectively, alkyl groups, as previously defined, attached to the parent molecular moiety through a nitrogen atom. The term alkylamino refers to a group having the structure —NHR' wherein R' is an alkyl group, as previously defined; whereas the term dialkylamino refers to a group having the structure —NR'R", wherein R' and R" are each independently selected from the group consisting of alkyl groups. The term trialkylamino refers to a group having the structure —NR'R"R'", wherein R', R", and R'" are each independently selected from the group consisting of alkyl groups. Additionally, R', R", and/or R'" taken together may optionally be —$(CH_2)_k$— where k is an integer from 2 to 6. Examples include, but are not limited to, methylamino, dimethylamino, ethylamino, diethylamino, diethylaminocarbonyl, methylethylamino, iso-propylamino, piperidino, trimethylamino, and propylamino.

The amino group is —NR'R", wherein R' and R" are typically selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

The terms alkylthioether and thioalkoxyl refer to a saturated (i.e., alkyl-S—) or unsaturated (i.e., alkenyl-S— and alkynyl-S—) group attached to the parent molecular moiety through a sulfur atom. Examples of thioalkoxyl moieties include, but are not limited to, methylthio, ethylthio, propylthio, isopropylthio, n-butylthio, and the like.

"Acylamino" refers to an acyl-NH— group wherein acyl is as previously described. "Aroylamino" refers to an aroyl-NH— group wherein aroyl is as previously described.

The term "carbonyl" refers to the —(C=O)— group.

The term "carboxyl" refers to the —COOH group. Such groups also are referred to herein as a "carboxylic acid" moiety.

The terms "halo," "halide," or "halogen" as used herein refer to fluoro, chloro, bromo, and iodo groups. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "hydroxyl" refers to the —OH group.

The term "hydroxyalkyl" refers to an alkyl group substituted with an —OH group.

The term "mercapto" refers to the —SH group.

The term "oxo" as used herein means an oxygen atom that is double bonded to a carbon atom or to another element.

The term "nitro" refers to the —$NO_2$ group.

The term "thio" refers to a compound described previously herein wherein a carbon or oxygen atom is replaced by a sulfur atom.

The term "sulfate" refers to the —$SO_4$ group.

The term thiohydroxyl or thiol, as used herein, refers to a group of the formula —SH.

The term ureido refers to a urea group of the formula —NH—CO—$NH_2$.

Unless otherwise explicitly defined, a "substituent group," as used herein, includes a functional group selected from one or more of the following moieties, which are defined herein:

(A) —OH, —$NH_2$, —SH, —CN, —$CF_3$, —$NO_2$, oxo, halogen, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, and heteroaryl, substituted with at least one substituent selected from:

(i) oxo, —OH, —$NH_2$, —SH, —CN, —$CF_3$, —$NO_2$, halogen, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, and heteroaryl, substituted with at least one substituent selected from:

(a) oxo, —OH, —$NH_2$, —SH, —CN, —$CF_3$, —$NO_2$, halogen, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, or heteroaryl, substituted with at least one substituent selected from oxo, —OH, —$NH_2$, —SH, —CN, —$CF_3$, —$NO_2$, halogen, unsubstituted alkyl, unsubstituted heteroalkyl, unsubstituted cycloalkyl, unsubstituted heterocycloalkyl, unsubstituted aryl, and unsubstituted heteroaryl.

A "lower substituent" or "lower substituent group," as used herein means a group selected from all of the substituents described hereinabove for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_5$-$C_7$ cycloalkyl, and each substituted or unsubstituted heterocycloalkyl is a substituted or unsubstituted 5 to 7 membered heterocycloalkyl.

A "size-limited substituent" or "size-limited substituent group," as used herein means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_4$-$C_8$ cycloalkyl, and each substituted or unsubstituted heterocycloalkyl is a substituted or unsubstituted 4 to 8 membered heterocycloalkyl.

Throughout the specification and claims, a given chemical formula or name shall encompass all tautomers, congeners, and optical- and stereoisomers, as well as racemic mixtures where such isomers and mixtures exist.

Certain compounds of the present disclosure possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present disclosure. The compounds of the present disclosure do not include those which are known in art to be too unstable to synthesize and/or isolate. The present disclosure is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefenic bonds or other centers of geometric asymmetry, and unless specified otherwise, it is intended that the compounds include both E and Z geometric isomers.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

It will be apparent to one skilled in the art that certain compounds of this disclosure may exist in tautomeric forms, all such tautomeric forms of the compounds being within the scope of the disclosure. The term "tautomer," as used herein, refers to one of two or more structural isomers which exist in equilibrium and which are readily converted from one isomeric form to another.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of this disclosure.

The compounds of the present disclosure may also contain unnatural proportions of atomic isotopes at one or more of atoms that constitute such compounds. For example, the compounds may be radiolabeled with radioactive isotopes, such as for example tritium ($^{3}H$), iodine-125 ($^{125}I$) or carbon-14 ($^{14}C$). All isotopic variations of the compounds of the present disclosure, whether radioactive or not, are encompassed within the scope of the present disclosure.

The compounds of the present disclosure may exist as pharmaceutically acceptable salts. The term "pharmaceutically acceptable salts" is meant to include salts of active compounds which are prepared with relatively nontoxic acids or bases, depending on the particular substituent moieties found on the compounds described herein. Pharmaceutically acceptable salts are generally well known to those of ordinary skill in the art, and may include, by way of example but not limitation, acetate, benzenesulfonate, besylate, benzoate, bicarbonate, bitartrate, bromide, calcium edetate, carnsylate, carbonate, citrate, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, mucate, napsylate, nitrate, pamoate (embonate), pantothenate, phosphate/diphosphate, polygalacturonate, salicylate, stearate, subacetate, succinate, sulfate, tannate, tartrates, (e.g. (+)-tartrates, (−)-tartrates or mixtures thereof including racemic mixtures), or teoclate. These salts may be prepared by methods known to those skilled in art. Other pharmaceutically acceptable salts may be found in, for example, Remington: The Science and Practice of Pharmacy ($20^{th}$ ed.) Lippincott, Williams & Wilkins (2000).

Also included are base addition salts such as sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent. Examples of acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like.

Also included are salts of amino acids such as arginate and the like, and salts of organic acids like glucuronic or galactunoric acids and the like, see, for example, Berge et al, "Pharmaceutical Salts", Journal of Pharmaceutical Science, 1977, 66, 1-19). Certain specific compounds of the present disclosure contain both basic and acidic functionalities that allow the compounds to be converted into either base or acid addition salts. The neutral forms of the compounds may be regenerated by contacting the salt with a base or acid and isolating the parent compound in the conventional manner. The parent form of the compound differs from the various salt forms in certain physical properties, such as solubility in polar solvents.

Certain compounds of the present disclosure can exist in unsolvated forms as well as solvated forms, including hydrated forms. In general, the solvated forms are equivalent to unsolvated forms and are encompassed within the scope of the present disclosure. Certain compounds of the present disclosure may exist in multiple crystalline or amorphous forms. In general, all physical forms are equivalent for the uses contemplated by the present disclosure and are intended to be within the scope of the present disclosure.

In addition to salt forms, the present disclosure provides compounds, which are in a prodrug form. Prodrugs of the compounds described herein are those compounds that readily undergo chemical changes under physiological conditions to provide the compounds of the present disclosure. Additionally, prodrugs can be converted to the compounds of the present disclosure by chemical or biochemical methods in an ex vivo environment. For example, prodrugs can be slowly converted to the compounds of the present disclosure when placed in a transdermal patch reservoir with a suitable enzyme or chemical reagent.

D. General Definitions

Although specific terms are employed herein, they are used in a generic and descriptive sense only and not for purposes of limitation. Unless otherwise defined, all technical and scientific terms used herein have the same meaning as commonly understood by one of ordinary skill in the art to which this presently described subject matter belongs.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, parameters, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The synthetic descriptions and specific examples that follow are only intended for the purposes of illustration, and are not to be construed as limiting in any manner to make compounds of the disclosure by other methods.

Example 1

General Methods

All chemical reactions, unless otherwise stated, were carried out under a nitrogen or argon atmosphere in anhydrous, freshly distilled solvents. Commercially available compounds were purchased from Sigma-Aldrich (St. Louis, Mo.) or Alfa-Aesar (Ward Hill, Mass.) and were used without further purification. All $^1$H and $^{13}$C nuclear magnetic resonance (NMR) spectra were acquired on a Bruker 300 or 400 MHz spectrometer and are reported in parts per million (δ) referenced against a TMS standard or solvent residual peak Infrared (IR) spectra were acquired on a Varian Vector 22 infrared spectrometer. Melting points were determined on a Thomas-Hoover capillary melting point apparatus and are uncorrected. Specific rotations were measured using a Jasco P-1010 polarimeter with pathlength and compound concentration indicated. Column chromatography was carried out on silica gel 60 (Merck, 230-400 mesh ASTM). Nominal masses were acquired with a Finnigan LCQ ion trap mass spectrometer with electrospray ionization. Masses were normalized to an external standard of Ampicillin. Exact masses were determined at the Johns Hopkins Mass Spectrometry Laboratory (Baltimore, Md.) or Old Dominion University College of Sciences Major Instrument Cluster (Norfolk, Va.). Water used for media and buffers was deionized with Barnstead/Thermolyne HN Ultrapure and HN Organic Rem. cartridges then distilled. E. coli DH5α was used for routine DNA manipulations and E. coli Rosetta2 (DE3) (Novagen) was used for overexpression of the thnG, thnQ and carC genes. Vector pET29b was purchased from Novagen. DNA purification was performed with QIAquick Gel Extraction or PCR Purification kits from Qiagen. Ni-NTA resin (Qiagen), desalting columns (Bio-Rad), Amicon Ultra 10,000 MWCO (Millipore), Bradford reagent (Bio-Rad), Lysozyme (Roche), Herculase DNA polymerase (Stratagene), PfuTurbo DNA polymerase (Stratagene), T4 DNA ligase (New England Biolabs (NEB)), Antarctic Phosphatase (NEB), NdeI (NEB) and XhoI (NEB) were purchased from the indicated suppliers. Sonication was performed with an Ultrasonic Processor GEX 400. DNA sequencing was performed at The Synthesis and Sequencing Facility at The Johns Hopkins University School of Medicine (Baltimore, Md.).

Example 2

PCR Amplification of thnG and thnQ and Ligation into pET29b

Genes thnG and thnQ were amplified from *Streptomyces cattleya* genomic DNA (PCR primers: thnQ; 5'-GC-CAAGCTTTCACCCGCCGCGGACCAG-3' forward (SEQ ID NO:1) and 5'-CACTAACTCGAGCCCGCCGCGGAC-CAGGTC-3' reverse (SEQ ID NO:2). thnG; 5'-CTAGTCTA-GAGGGCCTCCTCGGCGGAGAAG-3' forward (SEQ ID NO:3) and 5'-TTATAAGCTTTGGCCATGGTGAACG-GCTG-3' reverse (SEQ ID NO:4)) including terminal NdeI and XhoI sites. The PCR reactions (50 µL) contained 5 µL 10× Hi-Fi Taq buffer, 1 µL 10-mM dNTPs, 3 µL template (200 ng/µL *Streptomyces cattleya* genomic DNA), 1 µL 10-pmol/µL each primer and 0.5 µL Herculase (ThnG) or PfuTurbo (ThnQ). The reactions were heated at 96° C. for 5 min followed by 5×/30× cycles of 45 s at 96° C., 60° C./73° C. for 30 s, 72° C. for 2 min with a final extension of 72° C. for 7 min (ThnG) or 3×/30× cycles of 45 s at 96° C., 57° C./75° C. for 30 s, 72° C. for 2 min with a final extension of 72° C. for 7 min (ThnQ). After gel purification, the constructs were digested with NdeI and XhoI and ligated into the same sites of Antarctic Phosphatase-treated pET29b to give the genes with a C-terminal His6-tag. The plasmid was then transformed into DH5α competent cells and sequence-verified.

Example 3

Protein Expression

*E. coli* Rosetta2(DE3) was transformed with pET29b/thnG (Q), then grown overnight at 37° C. in LB medium (10 mL) supplemented with kanamycin (50 µg/mL) and chloramphenicol (30 µg/mL). The overnight culture was pelleted by centrifugation and the cells were resuspended in fresh medium then used to inoculate fresh LB medium (1 L) supplemented with the same antibiotic. Bacterial growth proceeded at 37° C. until the OD600 reached 0.6. The medium was cooled at 4° C. for 15 min then supplemented with 150 mg/L ferrous ammonium sulfate. Protein expression was induced by adding IPTG to reach a final concentration of 1 mM. After approximately 20 hours at 18° C., the cells were collected by centrifugation (4,000×g 15 min), then flash frozen in liquid nitrogen and stored at −80° C.

Example 4

Protein Purification

Frozen cells were thawed and resuspended on ice in 50 mM sodium phosphate pH 8.0, 300 mM NaCl, 10% glycerol (1 g cells/4 mL buffer). The cells were treated with Lysozyme (1 mg/mL) for 30 min then disrupted by sonication (40% amplitude micro-tip 4×9.9 s pulse, 9.9 s rest). Cell debris was cleared with centrifugation (25,000×g, 4° C., 30 min), and the cleared lysate was rotated on ice with Ni-NTA resin (1 mL resin/10 mL lysate) for 1 h. The suspension was loaded onto a column and washed with the lysis buffer and lysis buffer containing 20 mM imidazole (10 mL/1 mL Ni-NTA resin). The desired protein was eluted with lysis buffer containing 250 mM imidazole (9 mL/1 mL Ni-NTA resin). Fractions containing the desired protein were buffer exchanged with a desalting column (Bio-RAD) into 25 mM MOPS, pH 7.0, 10% glycerol and concentrated with centrifugation in an Amicon Ultra 10,000 MWCO filter (4,000×g, 5-15 min spins), until the protein concentration was >10 mg/mL, as determined by the Bradford method. The protein was frozen in liquid nitrogen and stored at −80° C.

Example 5

Cell-free Extracts

Frozen cells were thawed and resuspended in 50 mM MOPS pH 7.0, 25% glycerol (1 g cells/4 mL buffer). The cells were treated with Lysozyme (1 mg/mL) for 30 min then disrupted by sonication (40% amplitude micro-tip 4×9.9 s pulse, 9.9 s rest). Cell debris was cleared with centrifugation (25,000×g, 4° C., 30 min), to give the cell free extract.

Example 6

In VITRO Reactions with Purified ThnG and ThnQ

For routine HPLC analysis, reactions were assembled containing 25 mM MOPS, pH 7.0, 1 mM ascorbate, 0.08 mM ferrous ammonium sulfate, 8 mM α-ketoglutarate (α-KG), 1 mM of the substrate and 0.2 mg/mL ThnG or ThnQ. Salowe, S. P., et al., *Biochemistry* 29(27):6499-6508 (1990). After addition of the protein, the reactions were incubated at room temperature for 1 h. The protein was then removed with an Amicon Ultra 10,000 MWCO filter. For ESI mass spectroscopic analysis of HPLC purified enzymatic products, reactions were assembled under similar conditions except containing 2 mM substrate, 2 mM ascorbate and 0.6 mg/mL ThnG or ThnQ.

Example 7

In Vitro Reactions with Cell-free Extracts Harboring ThnG or ThnQ and Bioassay

Cell free extract harboring either ThnG or ThnQ (50 µL) was added to a solution containing 50 mM MOPS pH 7.0, 25% glycerol, 1 mM ascorbate, 0.08 mM ferrous ammonium sulfate, 8 mM α-KG, 2 mM of the substrate to give a final volume of 500 µL. After incubation for 2 h at room temperature, 200 µL of the reaction was analyzed with the supersensitive *E. coli* SC 12155, and by Nitrocefin β-lactamase induction assay with *Bacillus licheniformis* ATCC 14580. Sykes, R. B.; Wells, J. S., *J. Antibiot.* 38(1):119-121 (1985); Gerratana, B., et al., *Biochemistry* 42 (25):7836-7847 (2003).

Example 8

HPLC and ESI Mass Spectroscopic Analysis of ThnG and ThnQ Reactions with Carbapenams/ems HPLC conditions: Phenomenex Luna 5µ C18(2) analytical column; Method 1, A=50 mM ammonium formate pH 8.5, B=MeOH, t=0 min 0% B, t=10 min 35% B, t=13 min 35% B, t=15 min 0% B, t=20 min 0% B. Method 2, A=50 mM ammonium formate pH 8.5, B=MeOH, t=0 min 0% B, t=10 min 33% B, t=18 min 33% B, t=20 min 0% B, t=25 min 0% B.

$\lambda$=300 nm (carbapenem) or 220 nm (carbapenam). Decristoforo, G., *Anal. Chim. Acta* 163:25-33 (1984). Purified carbapenems were collected from the HPLC and analyzed directly by ESI mass spectrometry in the negative ion mode.

Example 9

Synthesis of Carbapenam/ems (2S,5S)-Carbapenam (11), (2S,5R)-carbapenam (12), and carbapenam thioethers (14, 15) were synthesized using established methods. Stapon, A., et al., *J. Am. Chem. Soc.* 125(51):15746-15747 (2003); Freeman, M. F., et al., *Proc. Natl. Acad. Sci.* 105(32):11128-11133 (2008). PS-5 (5), PS-7 (7) and (8S,R)-N-acetyl thienamycin (4) were synthesized using a slight modification of the method of Reider where the azetidinone derived from L-aspartic acid was alkylated with iodoethane or acetaldehyde. Finke, P. E., et al., *J. Med. Chem.* 38:(13), 2449-2462 (1995); Reider, P. J.; Grabowski, E. J. J., *Tetrahedron Lett.* 23(22):2293-2296 (1982).

The C-3 substituted azetidinones were converted to carbapenems by the method of Salzmann. Salzmann, T. N., et al., *J. Am. Chem. Soc.* 102(19):6161-6163 (1980); Ueda, Y., et al., *Can. J. Chem.* 62(12):2936-2940 (1984). For PS-5 (5) and (8S,R)-N-acetyl thienamycin (4), N-acetyl cysteamine was employed to give the C-2 moiety. Hart, D. J., et al., *J. Am. Chem. Soc.* 108(19):6054-6056 (1986); Bateson, J. H., et al., *J. Chem. Soc. Perkin Trans.* 1 (6):1793-1801 (1990); Corbett, D. F., et al.; *J. Chem. Soc. Perkin Trans.* 1 (12):3011-3016 (1982).

For PS-7 (7) silver (E)-2-acetamido-1-ethenethiolate was used. Natsugari, H., et al., *J. Chem. Soc. Perkin Trans.* 1 (2):403-411 (1983); Baxter, A. J. G., et al., *J. Chem. Soc. Chem. Comm.* (10):429-431 (1980). For the PS-5 sulfoxide diasteriomers (8) and PS-7 sulfoxide diasteriomers (9), the carbapenem carboxylic acid was oxidized with m-CPBA. Iimori, T., et al., *J. Am. Chem. Soc.* 105(6):1659-1660 (1983).

In the synthesis of 5-epi-PS-5 (6), and N-acetyl thienamycin (2) a catalytic asymmetric route to carbapenems was employed. Bodner, M. J., et al., *Org. Lett.* 11(16):3606-3609 (2009). Ethyl thioethers (16-17) also were prepared using this method of azetidinone formation and previously reported methods of carbapenam thioether formation. Freeman, M. F., et al., *Proc. Natl. Acad. Sci.* 105(32):11128-11133 (2008). Carbapenam/ems were prepared as the commonly used p-nitrobenzyl esters, which were readily removed by catalytic hydrogenation to afford the natural products or potential biosynthetic precursors. Hart, D. J., et al., *J. Am. Chem. Soc.* 108(19):6054-6056 (1986); Corbett, D. F., et al., *J. Chem. Soc. Perkin Trans.* 1 (12):3011-3016 (1982); Favara, D., et al., *Tetrahedron Lett.* 23(30):3105-3108 (1982); Corbett, D. F.; Eglington, A. J., *J. Chem. Soc. Chem. Comm.* (22):1083-1084 (1980).

p-Nitrobenzyl PS-5 (5a): p-Nitrobenzyl PS-5 (5a) was synthesized using established methods. Finke, P. E., et al., *J. Med. Chem.* 38(13):2449-2462 (1995); Reider, P. J.; Grabowski, E. J. J., *Tetrahedron Lett.* 23(22):2293-2296 (1982); Salzmann, T. N., et al. *J. Am. Chem. Soc.* 102(19):6161-6163 (1980); Ueda, Y., et al., *Can. J. Chem.* 62(12):2936-2940 (1984); Hart, D. J., et al., *J. Am. Chem. Soc.* 108(19):6054-6056 (1986). Recrystallization from acetonitrile afforded light yellow needles, m.p. 149-150° C.; $^1$H NMR (400 MHz, CDCl$_3$) δ 1.07 (t, J=7.6 Hz, 3H), 1.81-1.93 (m, 2H), 1.99 (s, 3H), 2.93 (m, J=6.4 Hz, 1H), 3.04 (m, J=6.4 Hz, 1H), 3.08 (dd, J=8.4, 18.0 Hz, 1H), 3.14 (dt, J=2.4, 6.8 Hz, 1H), 3.38-3.49 (m, 3H), 3.99 (apparent dt, J=2.4, 8.4 Hz, 1H), 5.38 (qab J=14.0 Hz, 2H), 5.99 (brs, 1H), 7.66 (d, J=8.8 Hz, 2H), 8.21 (d, J=8.8 Hz, 2H); $^{13}$C NMR (100 MHz, CDCl$_3$) δ 11.47, 22.44, 23.09, 31.59, 40.03, 40.41, 55.03, 61.42, 65.08, 123.68, 123.92, 128.00, 143.11, 147.50, 148.02, 160.81, 170.60, 178.69; [α]24D+65.0° (c 0.5, CH$_2$Cl$_2$); IR (CH$_2$Cl$_2$) 3300, 2970, 1770, 1660, 1520 cm$^{-1}$; HRMS (FAB/M+Na+), C$_{20}$H$_{23}$N$_3$O$_6$SNa requires m/e 456.1200, found 456.1201.

p-Nitrobenzyl PS-7 (7a): p-Nitrobenzyl PS-7 (7a) was synthesized as p-nitrobenzyl PS-5 (5a) except that the C-2 moiety was introduced using Ohno's method. Iimori, T., et al., *J. Am. Chem. Soc.* 105(6):1659-1660 (1983). Recrystallization from ethyl acetate and hexanes gave a fine white powder, m.p. 112-113° C.; $^1$H NMR (400 MHz, CDCl$_3$) δ 1.05 (t, J=7.6 Hz, 3H), 1.82 (m, J=7.2 Hz, 1H), 1.88 (m, J=7.2 Hz, 1H), 2.08 (s, 3H), 3.01 (dd, J=18.4, 8.0 Hz, 1H), 3.12 (dt, J=7.2, 2.4 Hz, 1H), 3.18 (dd, J=18.4, 9.6 Hz, 1H), 3.94 (m, J=8.0, 2.4 Hz, 1H), 5.38 (qab, J=13.6 Hz, 2H), 5.90 (d, J=13.6 Hz, 1H), 7.21 (d, J=13.6 Hz, 1H), 7.63 (brs, 1H), 7.65 (d, J=8.8 Hz, 2H), 8.21 (d, J=8.8 Hz, 2H); $^{13}$C NMR (100 MHz, CDCl$_3$) δ 11.55, 22.42, 23.24, 41.37, 54.94, 61.36, 65.15, 98.77, 122.48, 123.73, 128.08, 133.58, 143.10, 147.54, 149.90, 160.72, 167.37, 178.82; [α]24D+19.8° (c 0.5, CH$_2$Cl$_2$); IR (CH$_2$Cl$_2$) 3280, 2970, 1770, 1700, 1620, 1520 cm$^{-1}$; HRMS (FAB/M+H+), C$_{20}$H$_{21}$N$_3$O$_6$S requires m/e 431.1151, found 431.1146.

PS-5 Sulfoxide diasteriomers (8): PS-5 (5) was oxidized in quantitative yield using the procedure of Natsugari and analyzed by HPLC (method 2) and ESI mass spectrometry (C$_{13}$H$_{17}$N$_2$O$_5$S— theoretical (m/z 313.09), observed (m/z 313.04). Natsugari, H., et al., *J. Chem. Soc. Perkin Trans.* 1(2):403-411 (1983).

PS-7 Sulfoxide diasteriomers (9): PS-7 (7) was oxidized in quantitative yield using the procedure of Natsugari and analyzed by HPLC (method 2) and ESI mass spectrometry C$_{13}$H$_{15}$N$_2$O$_4$S— theoretical (m/z 311.07), observed (m/z 311.04). Natsugari, H., et al., *J. Chem. Soc. Perkin Trans.* 1(2):403-411 (1983).

(3R, 4R)-Benzyl 3-(ethyl)-azetidin-2-one-4-carboxylate (19): N-Tosyl azetidinone 18 was detosylated as described by Bodner et al. and purified with flash chromatography on silica gel, 30% ethyl acetate in hexanes eluted a colorless oil in 81% yield. Bodner, M. J., et al., *Org. Lett.* 11(16):3606-3609 (2009). $^1$H NMR (400 MHz, CDCl$_3$) δ 0.97 (t, J=6.4 Hz, 3H), 1.55 (m, J=6.4 Hz, 1H), 1.66 (m, J=6.4 Hz, 1H), 3.44 (dt, J=6.0, 6.4 Hz, 1H), 4.30 (d, J=6.0 Hz, 1H), 5.21 (s, 2H), 6.01 (brs, 1H), 7.38 (brs, 5H); $^{13}$C NMR (100 MHz, CDCl$_3$) δ 11.53, 19.36, 52.35, 56.92, 67.31, 128.64, 128.72, 128.78, 134.83, 169.88, 170.24; IR (CH$_2$Cl$_2$) 3290, 2970, 1750 cm$^{-1}$; [α]23D+46.4° (c 0.75, CH$_2$Cl$_2$); HRMS (FAB/M+Na+), C13H15NO3Na requires m/e 256.0944, found 256.0939.

(3R,4R)-Benzyl-N-(tert-butyldimethylsilyl)-3-(ethyl)-azetidin-2-one-4-carboxylate(20): Azetidinone 19 was silated as described by Bodner et al. and purified with flash chromatography on silica gel, 10% ethyl acetate in hexanes eluted a colorless oil, 92% yield. Bodner, M. J., et al., *Org. Lett.* 11(16):3606-3609 (2009). $^1$H NMR (400 MHz, CDCl$_3$) δ 0.05 (s, 3H), 0.27 (s, 3H), 0.93 (t, J=7.2 Hz, 3H), 0.94 (s, 9H), 1.45 (m, J=7.2 Hz, 1H), 1.66 (m, J=7.2 Hz, 1H), 3.44 (dt, J=6.4, 6.0 Hz, 1H), 4.20 (d, J=6.0 Hz, 1H), 5.19 (qab, J=12.0 Hz, 2H), 7.38 (brs, 5H); $^{13}$C NMR (100 MHz, CDCl$_3$) δ −6.30, −5.81, 11.71, 18.52, 19.11, 26.13, 54.10, 56.95, 67.09, 128.62, 128.69, 128.90, 134.94, 171.04, 174.36; IR (CH$_2$Cl$_2$) 2930, 1750 cm$^{-1}$; [α]22D+42.9° (c1.0, CH$_2$Cl$_2$); HRMS (FAB/M+H+), C$_{19}$H$_{30}$NO$_3$Si requires m/e 348.1995, found 348.1985.

(3R,4R)-N-(tert-Butyldimethylsilyl)-3-(ethyl)azetidin-2-one-4-carboxylate (21): Azetidinone 20 was hydrogenated as described by Bodner et al. to give a white solid that was triturated in pentane to give a white powder, 99% yield. Bodner, M. J., et al., *Org. Lett.* 11(16):3606-3609 (2009). m.p. 134-135° C.; $^1$H NMR (400 MHz, CDCl$_3$) δ 0.14 (s, 3H), 0.32 (s, 3H), 0.97 (s, 9H), 1.05 (t, J=7.6 Hz, 3H), 1.62 (m, J=7.6 Hz, 1H), 1.77 (m, J=7.6 Hz, 1H), 3.54 (dt, J=7.6, 6.0 Hz, 1H), 4.23 (d, J=6.0 Hz, 1H); $^{13}$C NMR (100 MHz, CDCl$_3$) δ −6.52, −6.06, 11.44, 18.34, 18.87, 26.00, 53.97, 55.97, 173.90, 175.88; IR (CH$_2$Cl$_2$) 2930, 1740, 1730 cm$^{-1}$ [α]22D+68.1° (c 0.38, CH$_2$Cl$_2$); HRMS (FAB/M+H+), C$_{12}$H$_{24}$NO$_3$Si requires m/e 258.1526, found 258.1529.

(3R,4R)-N-(tert-Butyldimethylsilyl)-4-diazoacetyl-3-(ethyl)-azetidin-2-one (22): Azetidinone acid 21 was converted to the diazoketone as described by Bodner et al. to give a light yellow solid in quantitative yield and suitable purity to be used directly; or, if desired, could be further purified by dissolving in hot hexanes, filtering through Celite to remove any insoluble material, and then crystallized. Bodner, M. J., et al., *Org. Lett.* 11(16):3606-3609 (2009). An analytical sample was purified by flash chromatography on silica gel eluted with 20% ethyl acetate in hexanes to afford a light yellow solid (34% recovery); recrystallization from hot hexanes gave pale yellow needles, m.p. 88-89° C.; $^1$H NMR (400 MHz, CDCl$_3$) δ 0.07 (s, 3H), 0.30 (s, 3H, 0.93 (s, 9H), 0.98 (t, J=7.6 Hz, 3H), 1.51 (m, J=7.6 Hz, 1H), 1.68 (m, J=7.6 Hz, 1H), 3.43 (m, J=7.6 Hz, 1H), 4.09 (d, J=6.0 Hz, 1H), 5.50 (brs, 1H); $^{13}$C NMR (100 MHz, CDCl$_3$) δ −6.41, −5.95, 11.71, 18.23, 18.60, 25.89, 54.42, 57.00, 58.16, 174.42, 191.90; IR (CH$_2$Cl$_2$) 2900, 2100, 1740, 1650 cm$^{-1}$ [α]21D+86.0° (c 0.38, CH$_2$Cl$_2$); HRMS (FAB/M+H+), C$_{13}$H$_{24}$N$_3$O$_2$Si requires m/e 282.1638, found 282.1628.

(3R,4S)-N-(tert-Butyldimethylsilyl)-3-(ethyl)-azetidin-2-one-yl-acetic acid (23): Diazoketone 22 underwent the Wolff rearrangement in 10% aqueous THF as described by Bodner et al. to give a yellow solid, which was triturated in pentane to give a light yellow powder in 96% yield. Bodner, M. J., et al., *Org. Lett.* 11(16):3606-3609 (2009). m.p. 94-96° C.; $^1$H NMR (400 MHz, CDCl$_3$) δ 0.16 (s, 3H), 0.18 (s, 3H), 0.89 (s, 9H), 0.99 (t, J=7.2 Hz, 3H), 1.50 (m, J=7.2 Hz, 1H), 1.62 (m, J=7.2 Hz, 1H), 2.54 (dd, J=17.2, 10.0 Hz, 1H), 2.68 (dd, J=17.2, 4.0 Hz, 1H), 3.24 (dt, J=10.0, 6.0 Hz, 1H), 4.05 (m, 1H); $^{13}$C NMR (100 MHz, CDCl$_3$) δ −5.78, −5.54, 12.10, 18.28, 18.31, 26.11, 35.92, 49.63, 54.98, 174.79, 176.75; IR (CH$_2$Cl$_2$) 2930, 1725, 1680 cm$^{-1}$ [α]22D+44.6° (c 1.0, CH$_2$Cl$_2$); HRMS (FAB/M+H+), C$_{13}$H$_{26}$NO$_3$Si requires m/e 272.1682, found 272.1681.

p-Nitrobenzyl 4-((3R, 4S)-3-(ethyl))-2-azetidinon-4-yl)-3-oxo-2-diazobutanoate (24): Homologated acid 23 was coupled with magnesium mono-p-nitrobenzyl malonate, diazotized and desilated as described by Bodner et al. It was purified by flash chromatography on silica gel eluting with 50-80% ethyl acetate in hexanes to give a colorless oil in 33% yield. Bodner, M. J., et al., *Org. Lett.* 11(16):3606-3609 (2009). $^1$H NMR (400 MHz, CDCl$_3$) δ 1.04 (t, J=7.2 Hz, 3H), 1.55 (m, J=7.2 Hz, 1H), 1.73 (m, J=7.2 Hz, 1H), 2.97 (dd, J=18.0, 9.6 Hz, 1H), 3.16 (m, J=7.2 Hz, 1H), 3.23 (dd, J=18.0, 3.6 Hz, 1H), 4.06 (m, J=4.0 Hz, 1H), 5.35 (s, 2H), 6.29 (brs, 1H), 7.53 (d, J=8.8 Hz, 2H), 8.22 (d, J=8.8 Hz, 2H); $^{13}$C NMR (100 MHz, CDCl$_3$) δ 12.29, 18.46, 41.47, 47.17, 54.48, 65.46, 123.88, 128.66, 141.92, 147.89, 160.56, 170.98, 190.19; IR (CHCl$_3$) 3350, 2970, 2140, 1730, 1710, 1650, 1520 cm$^{-1}$; [α]22D −37.6° (c 1.0, CHCl$_3$); HRMS (FAB/M+H+), C$_{16}$H$_{17}$N$_4$O$_6$Si requires m/e 361.1148, found 361.1144.

p-Nitrobenzyl 5-epi-PS-5 (6a): Azetidinone 24 was converted to the carbapenem by the procedure of Salzmann to give a white solid in 43% yield. Salzmann, T. N., et al., *J. Am. Chem. Soc.* 102(19):6161-6163 (1980). It was recrystallized from CH$_3$CN to give colorless leaves, m.p. 138-139° C. $^1$H NMR (400 MHz, CDCl$_3$) δ 1.04 (t, J=7.2 Hz, 3H), 1.62 (m, J=7.2, 2.0 Hz, 1H), 1.85 (m, J=7.2 Hz, 1H), 1.99 (s, 3H), 2.96 (m, J=7.2 Hz, 1H), 3.06 (dd, J=18.0, 9.6 Hz, 1H), 3.09 (m, J=7.2 Hz, 1H), 3.22 (dd, J=18.0, 9.6 Hz, 1H), 3.42 (m, J=7.2 Hz, 1H), 3.52 (m, J=7.2 Hz, 1H), 3.57 (m, J=7.2 Hz, 1H), 4.31 (dt, J=9.6, 6.0 Hz, 1H), 5.37 (qab, J=13.6 Hz, 2H), 5.96 (brs, 1H), 7.65 (d, J=8.8 Hz, 2H), 8.22 (d, J=8.8 Hz, 2H); $^{13}$C NMR (100 MHz, CDCl$_3$) δ 11.81, 18.83, 23.14, 31.73, 35.42, 39.93, 53.56, 54.49, 65.10, 118.04, 123.73, 128.03, 143.08, 148.63, 160.82, 170.52, 175.57, 179.21; IR (CHCl$_3$) 3280, 3080, 2960, 1770, 1700, 1660, 1600 cm$^{-1}$; [α]22D −9.7° (c 0.5, CH$_2$Cl$_2$); HRMS (FAB/M+Na+), C$_{20}$H$_{23}$N$_3$O$_6$SNa requires m/e 456.1200, found 456.1201.

5-epi-PS-5 (6): p-Nitrobenzyl 5-epi-PS-5 (6a) was deprotected by the procedure of Corbett to give a white powder. Corbett, D. F., et al., *J. Chem. Soc. Perkin Trans.* 1(12):3011-3016 (1982). $^1$H NMR (400 MHz, CDCl$_3$) δ 0.97 (t, J=7.2 Hz, 3H), 1.63 (m, J=7.2 Hz, 1H), 1.76 (m, J=7.2, 1H), 2.00 (s, 3H), 2.93 (m, 1H), 3.05 (m, 3H), 3.42 (m, 2H), 3.59 (m, 1H), 4.30 (dt, J=8.0, 4.8, 1H).

(5S,6R) p-Nitrobenzyl 6-ethylcarbapenem (25): Azetidinone 24 was converted to the C-2 unsubstituted carbapenem as described by Freeman to give a white solid. Freeman, M. F., et al., *Proc. Natl. Acad. Sci.* 105(32):11128-11133 (2008). Recrystallization from ethyl acetate and hexanes gave a white powder in 49% yield. m.p. 140-141° C.; $^1$HNMR (400 MHz, CDCl$_3$) δ 1.02 (t, J=7.2 Hz, 3H), 1.63 (m, J=7.2, 2.0 Hz, 1H), 1.84 (m, J=7.2 Hz, 1H), 2.78 (m, 2H), 3.55 (dt, J=8.8, 7.2 Hz, 1H), 4.38 (dt, J=9.2, 6.0 Hz, 1H), 5.36 (qab, J=14.0 Hz, 2H), 6.14 (t, J=2.8 Hz, 1H), 7.61 (d, J=8.8 Hz, 2H), 8.22 (d, J=8.8 Hz, 2H); $^{13}$C NMR (100 MHz, CDCl$_3$) δ 11.75, 18.73, 30.81, 54.30, 55.57, 65.31, 123.73, 128.14, 133.35, 135.14, 138.47, 142.71, 160.12, 180.07; IR (CHCl$_3$) 2970, 1760, 1720 cm$^{-1}$; [α]23D −62.3° (c 1.9, CHCl$_3$); HRMS (FAB/M+H+), C$_{16}$H$_{17}$N$_2$O$_5$ requires m/e 317.1138, found 317.1133.

(2S,3R,5S,6R) p-Nitrobenzyl-2-(N-acetyl cysteaminyl)-6-ethylcarbapenam (26) and (2R,3R,5S,6R)p-Nitrobenzyl-2-(N-acetyl cysteaminyl)-6-ethylcarbapenam (27): N-Acetyl cysteamine was added to carbapenem 26, as described by Freeman. Freeman, M. F., et al., *Proc. Natl. Acad. Sci.* 105 (32):11128-11133 (2008). The resulting diasteriomeric mixture was separated by HPLC, Phenomonex Luna 5 silica (2) 100 A 250 10 mm 5 μm, 0.75% methanol in ethyl acetate mobile phase, observed at 265 nm, retention time (min): 27, 9.2; 26, 11.2. (26) colorless oil, 30% yield: $^1$H NMR (400 MHz, CDCl$_3$) δ 1.00 (t, J=7.2 Hz, 3H), 1.60 (m, J=7.2 Hz, 1H), 1.66 (m, 1H), 1.79 (m, J=7.2 Hz, 1H), 1.99 (s, 3H), 2.48 (m, J=6.4 Hz, 1H), 2.68 (m, J=6.8 Hz, 1H), 2.80 (m, J=6.8 Hz, 1H), 3.40 (m, 3H), 3.82 (dt, J=9.2, 6.4 Hz, 1H), 3.95 (dt, J=6.0, 8.4 Hz, 1H), 4.28 (d, J=6.4 Hz, 1H), 5.30 (s, 2H), 5.95 (brs, 1H), 7.55 (d, J=8.4 Hz, 2H), 8.24 (d, J=8.4 Hz, 2H); $^{13}$C NMR (100 MHz, CDCl$_3$) δ 11.81, 18.63, 23.18, 32.30, 34.04, 38.71, 50.93, 53.74, 56.77, 64.60, 65.82, 123.90, 128.37, 142.28, 147.91, 169.85, 170.25, 178.81; IR (CHCl$_3$) 3320, 2930, 1750, 1660, 1520 cm$^{-1}$; [α]24D −66.2° (c 0.4, CH$_2$Cl$_2$); HRMS (FAB/M+H+), C$_{20}$H$_{26}$N$_3$O$_6$S requires m/e 436.1542, found 436.1545.

(27) colorless oil; 30% yield: $^1$H NMR (400 MHz, CDCl$_3$) δ 1.04 (t, J=7.2 Hz, 3H), 1.48 (m, J=7.2 Hz, 1H), 1.66 (m, J=7.2 Hz, 1H), 1.99 (s, 3H), 2.03 (ddd, J=13.6, 5,2, 3.4 Hz, 1H), 2.25 (ddd, J=13.6, 8.0, 2.4 Hz, 1H), 2.68 (m, J=6.4 Hz, 1H), 2.70 (m, J=6.4 Hz, 1H), 3.38 (m, 4H), 4.17 (ddd, J=8.0, 5.2, 2.4 Hz, 1H), 4.73 (d, J=7.2 Hz, 1H), 5.30 (qab, J=13.2 Hz, 2H), 5.95 (brs, 1H), 7.56 (d, J=8.8 Hz, 2H), 8.25 (d, J=8.8 Hz, 2H); $^{13}$C NMR (100 MHz, CDCl$_3$) δ 11.88, 18.73, 23.02, 31.13, 33.23, 38.75, 49.45, 54.15, 56.34, 64.01, 65.54, 123.89, 128.79, 142.18, 148.05, 168.36, 170.13, 179.90; IR (CHCl$_3$) 3310, 2970, 1750, 1650, 1520 cm$^{-1}$; [α]24D −23.5° (c 0.4, CH$_2$Cl$_2$); HRMS (FAB/M+H+), C$_{20}$H$_{26}$N$_3$O$_6$S requires m/e 436.1542, found 436.1551.

(2S,3R,5S,6R)-2-(N-acetyl cysteaminyl)-6-ethylcarbapenam (16): (2S,3R,5S,6R) p-Nitrobenzyl-2-(N-acetyl cysteaminyl)-6-ethylcarbapenam (26) was deprotected by the procedure of Corbett to give a white powder. Corbett, D. F., et al., *J. Chem. Soc. Perkin Trans.* 1(12):3011-3016 (1982). $^1$H NMR (400 MHz, CDCl$_3$) δ 0.95 (t, J=7.2 Hz, 3H), 1.62 (m, 1H), 1.69 (m, 2H), 2.00 (s, 1H), 2.50 (m, 1H), 2.81 (m, 2H), 3.41 (m, 3H), 3.78 (dt, J=6.8 Hz, 1H), 4.04 (m, 2H).

(2R,3R,5S,6R)-2-(N-acetyl cysteaminyl)-6-ethylcarbapenam (27): (2R,3R,5S,6R) p-Nitrobenzyl-2-(N-acetyl cysteaminyl)-6-ethylcarbapenam (17) was deprotected by the procedure of Corbett to give a white powder. Corbett, D. F., et al., *J. Chem. Soc. Perkin Trans.* 1(12):3011-3016 (1982). $^1$H NMR (400 MHz, CDCl$_3$) δ 0.96 (t, J=7.2 Hz, 3H), 1.52 (m, 1H), 1.62 (m, 1H), 2.00 (s, 3H), 2.15 (t, J=6.4 Hz, 2H), 2.80 (m, 2H), 3.43 (m, 3H), 3.80 (dt, J=6.4 Hz, 1H), 4.20 (dt, J=6.4 Hz, 1H), 4.42 (d, J=6.8 Hz, 1H).

REFERENCES

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art.

Bateson, J. H.; Hickling, R. I.; Smale, T. C.; Southgate, R., *J. Chem. Soc. Perkin Trans.* 1 1990, (6), 1793-1801.

Baxter, A. J. G.; Ponsford, R. J.; Southgate, R., *J. Chem. Soc. Chem. Comm.* 1980, (10), 429-431.

Bodner, M. J.; Phelan, R. M.; Townsend, C. A., *Org. Lett.* 2009, 11, (16), 3606-3609.

Bonfiglio, G., Russo, G. and Nicoletti, G. *Expert Opin. Invest. Drugs* 2002, 11 (4) 529-544.

Corbett, D. F.; Eglington, A. J., *J. Chem. Soc. Chem. Comm.* 1980, (22), 1083-1084.

Corbett, D. F.; Coulton, S.; Southgate, R., *J. Chem. Soc. Perkin Trans.* 1 1982, (12), 3011-3016.

Decristoforo, G., *Anal. Chim. Acta* 1984, 163, 25-33.

Favara, D.; Omodeisale, A.; Consonni, P.; Depaoli, A., *Tetrahedron Lett.* 1982, 23, (30), 3105-3108.

Finke, P. E.; Shah, S. K.; Fletcher, D. S.; Ashe, B. M.; Brause, K. A.; Chandler, G. O.; Dellea, P. S.; Hand, K. M.; Maycock, A. L.; Osinga, D. G.; Underwood, D. J.; Weston, H.; Davies, P.; Doherty, J. B., *J. Med. Chem.* 1995, 38, (13), 2449-2462.

Freeman, M. F.; Moshos, K. A.; Bodner, M. J.; Li, R. F.; Townsend, C. A., *Proc. Natl. Acad. Sci.* 2008, 105, (32), 11128-11133.

Gerratana, B.; Stapon, A.; Townsend, C. A., *Biochemistry* 2003, 42, (25), 7836-7847.

Hamed, R. B., Batchelar, E. T., Mecinovic, J., Claridge, T. D. W. and Schofield, C. J. *ChemBioChem* 2009, 10 (2) 246-250;

Hart, D. J.; Lee, C. S.; Pirkle, W. H.; Hyon, M. H.; Tsipouras, A., *J. Am. Chem. Soc.* 1986, 108, (19), 6054-6056.

Hausinger, R. P. *Crit. Rev. Biochem. Mol.* 2004, 39 (1) 21-68.

Houck, D. R., Kobayashi, K., Williamson, J. M. and Floss, H. G. *J. Am. Chem. Soc.* 1986, 108 (17) 5365-5366.

Iimori, T.; Takahashi, Y.; Izawa, T.; Kobayashi, S.; Ohno, M., *J. Am. Chem. Soc.* 1983, 105, (6), 1659-1660.

Li, R. F., Stapon, A., Blanchfield, J. T. and Townsend, C. A. *J. Am. Chem. Soc.* 2000, 122 (38) 9296-9297.

McGowan, S. J., Sebaihia, M., Porter, L. E., Stewart, G. S. A. B., Williams, P., Bycroft, B. W. and Salmond, G. P. C. *Mol. Microbiol.* 1996, 22 (3) 415-426;

Natsugari, H.; Matsushita, Y.; Tamura, N.; Yoshioka, K.; Ochiai, M., *J. Chem. Soc. Perkin Trans.* 1 1983, (2), 403-411.

Nunez, L. E., Mendez, C., Brana, A. F., Blanco, G. and Salas, J. A. *Chem. Biol.* 2003, 10 (4) 301-311.

Reider, P. J.; Grabowski, E. J. J., *Tetrahedron Lett.* 1982, 23, (22), 2293-2296.

Rosi, D., Drozd, M. L., Kuhrt, M. F., Terminiello, L., Came, P. E. and Daum, S. J. *J. Antibiot.* 1981, 34 (3) 341-343.

Salowe, S. P.; Marsh, E. N.; Townsend, C. A., *Biochemistry* 1990, 29, (27), 6499-6508.

Salzmann, T. N.; Ratcliffe, R. W.; Christensen, B. G.; Bouffard, F. A., *J. Am. Chem. Soc.* 1980, 102, (19), 6161-6163.

Stapon, A.; Li, R. F.; Townsend, C. A., *J. Am. Chem. Soc.* 2003, 125, (51), 15746-15747.

Stapon, A., Li, R. F. and Townsend, C. A. *J. Am. Chem. Soc.* 2003, 125 (28) 8486-8493.

Sykes, R. B.; Wells, J. S., *J. Antibiot.* 1985, 38, (1), 119-121.

Ueda, Y.; Roberge, G.; Vinet, V., *Can. J. Chem.* 1984, 62, (12), 2936-2940.

Williamson, J. M., Inamine, E., Wilson, K. E., Douglas, A. W., Liesch, J. M. and Albersschonberg, G. *J. Biol. Chem.* 1985, 260 (8) 4637-4647;

Wilson, K. E., Kempf, A. J., Liesch, J. M. and Arison, B. H. *J. Antibiot.* 1983, 36 (9) 1109-1117.

Although the foregoing subject matter has been described in some detail by way of illustration and example for purposes of clarity of understanding, it will be understood by those skilled in the art that certain changes and modifications can be practiced within the scope of the appended claims.

That which is claimed:

1. A process for preparing a carbapenem of Formula (I):

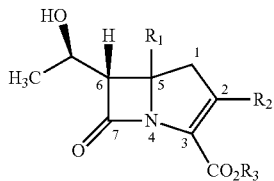

the process comprising contacting or incubating a carbapenem substrate of Formula (Ia):

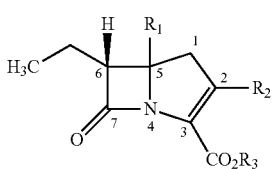

with a purified ThnQ enzyme that stereospecifically hydroxylates the C8 carbon atom of the carbapenem substrate of Formula (Ia) under reaction conditions to produce an optically-pure carbapenem of Formula (I);

wherein:

$R_1$ is H;

$R_2$ is selected from the group consisting of —SCH$_2$CH$_2$NH$_2$, —SCH=CHNHC(=O)CH$_3$, —S-pantethienyl, —SCH$_2$CH$_2$NHC(=O)R', wherein R' is $C_1$-$C_{10}$ substituted or unsubstituted linear or branched alkyl, which can be further substituted with one or more 3-6 member cycloalkyl rings, or aminoalkyl; and $R_3$ is H.

2. The process of claim 1, wherein $R_2$ is —SCH$_2$CH$_2$NHC(=O)R', and wherein the —C(=O)R' moiety is selected from the group consisting of glycyl, β-alanyl, 2-hydroxyacetyl, 2-methoxyacetyl, 3-hydroxypropionyl, 4-hydroxybutanoyl, and 3,4-dihydroxybutanoyl.

3. The process of claim 1, wherein the compound of Formula (I) is selected from the group consisting of: